US012733897B2

(12) United States Patent
Goftari et al.

(10) Patent No.: US 12,733,897 B2
(45) Date of Patent: Sep. 15, 2026

(54) ENTROPY BASED HEART SOUND TRACKING

(71) Applicant: Cardiac Pacemakers, Inc., St. Paul, MN (US)

(72) Inventors: Mojgan Goftari, Shoreview, MN (US); Jonathan Bennett Shute, Eagan, MN (US); Pramodsingh Hirasingh Thakur, Woodbury, MN (US); Viktoria A. Averina, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 246 days.

(21) Appl. No.: 18/536,659

(22) Filed: Dec. 12, 2023

(65) Prior Publication Data

US 2024/0197284 A1 Jun. 20, 2024

Related U.S. Application Data

(60) Provisional application No. 63/432,649, filed on Dec. 14, 2022.

(51) Int. Cl.
*A61B 5/00* (2006.01)
*A61B 5/024* (2006.01)
*A61B 7/02* (2006.01)

(52) U.S. Cl.
CPC ............ *A61B 7/02* (2013.01); *A61B 5/02444* (2013.01); *A61B 5/7282* (2013.01)

(58) Field of Classification Search
None
See application file for complete search history.

(56) References Cited

U.S. PATENT DOCUMENTS 10,660,577 B2 5/2020 Thakur et al.
2016/0106992 A1* 4/2016 Joo .................... A61N 1/39044 128/204.23

(Continued)

FOREIGN PATENT DOCUMENTS

CN 107480637 A 12/2017

OTHER PUBLICATIONS

Chidean, Mihaela I., et al., "Wireless Sensor Network for Low-Complexity Entropy Determination of Human Gait", See discussions, stats, and author profiles for this publication at: https://www.researchgate.net/publication/258114291, Conference Paper • Sep. 2013, DOI: 10.1109/PIMRC.2013.6666594, 6 pages.

(Continued)

*Primary Examiner* — Erica S Lee
(74) *Attorney, Agent, or Firm* — Nelson Mullins Riley & Scarborough LLP

(57) ABSTRACT

Systems and methods for recognizing and tracking heart sound components are disclosed. An exemplary medical-device system comprises a data receiver circuit to receive heart sound information, and a heart sound recognition circuit to generate a representative heart sound segment within a cardiac cycle, such as an ensemble average of a plurality of heart sound segments taken from multiple cardiac cycles. The heart sound recognition circuit can partition the representative heart sound segment into multiple heart sound data windows, calculate spectral entropy values respectively for each of the multiple heart sound data windows, and determine one or more heart sound components including an S2 component using the calculated spectral entropy values. A physiologic event detector can detect a cardiac event using the recognized one or more heart sound components.

20 Claims, 11 Drawing Sheets

(56) References Cited

U.S. PATENT DOCUMENTS

| | | | |
|---|---|---|---|
| 2017/0347968 A1 | 12/2017 | Maile et al. | |
| 2019/0343480 A1 * | 11/2019 | Shute | A61B 5/7203 |

OTHER PUBLICATIONS

International Preliminary Report on Patentability received for PCT Patent Application No. PCT/US2023/083502, mailed on Jun. 26, 2025, 8 pages.

International Search Report and Written Opinion received for PCT Patent Application No. PCT/US2023/083502, mailed on Apr. 10, 2024, 9 pages.

* cited by examiner

632

1000
2000
3000
4000
5000
6000
7000
8000
9000

5 10 15 20 25 30 35 40 45 50

640

642

1000
2000
3000
4000
5000
6000
7000
8000
9000

5 10 15 20 25 30 35 40 45 50

ENTROPY BASED HEART SOUND TRACKING

CLAIM OF PRIORITY

This application claims the benefit of U.S. Provisional Application No. 63/432,649, filed on Dec. 14, 2022, which is hereby incorporated by reference in its entirety.

TECHNICAL FIELD

This document relates generally to medical systems, and more particularly, to systems, devices and methods for recognizing and tracking heart sounds from a subject.

BACKGROUND

Heart sounds are generally associated with mechanical vibration of a heart and blood flow through the heart. Heart sounds recur with each cardiac cycle and are separated and classified according to the activity associated with the vibration. Historically, heart sounds were assessed by humans and thus only audible portion of the vibration was used. Devices can now assess full spectrum of cardiac vibrations which include both audible and subaudible components, thus the term "sound" in this document refers to the full spectrum of vibrations. Typically, heart sounds sensed from a subject may include several components within a cardiac cycle, including a first (S1), a second (S2), a third (S3), or a fourth (S4) heart sound. S1 is associated with the vibrations produced by the heart during tensing of the mitral valve. S2 is produced by closure of the aortic and pulmonary valves, and marks the beginning of diastole. S3 is produced by early diastolic vibrations corresponding to passive ventricular filling during diastole, when the blood rushes into the ventricles. S4 is produced by late diastolic vibrations corresponding to active ventricular filling when the atria contract and push the blood into the ventricles. In a healthy subject, S3 is usually faint and S4 is rarely audible. However, a pathologic S3 or S4 may be higher pitched and louder.

Heart sounds have been used to assess cardiac systolic and diastolic functions. Systole is the contraction or a period of contraction of the heart that causes blood to be forced out of the heart such as the ventricles and into the aorta and pulmonary artery. Diastole is the relaxation or a period of relaxation of the heart during which the blood flows back into the heart such as the ventricles. Patients with cardiac diseases may have deteriorated systolic or diastolic functions. For example, congestive heart failure (CHF) occurs when the heart is unable to supply enough blood to maintain a healthy physiologic state.

Implantable medical devices (IMDs) have been used to monitor patients with cardiac disease, such as to detect cardiac events leading to worsening heart failure (WHF). An IMD may sense physiologic signals from a patient, and deliver electrostimulation therapy to improve cardiac performance in CHF patients. Frequent patient monitoring via an IMD may help identify patients having an elevated risk of developing future heart failure events, ensure timely treatment, reduce heart failure hospitalization, improve patient outcome, and reduce healthcare cost.

OVERVIEW

An ambulatory medical device (AMD), such as an implantable medical device (IMD), a subcutaneous medical device, a wearable medical device, or other external medical device, may be used to monitor cardiac patient. An AMD may sense electrical or mechanical activities of the heart via sensing electrodes and/or physiologic sensors, and detect cardiac events such as cardiac arrhythmias or WHF. An IMD may include a pulse generator capable of generating and delivering electrostimulation therapy to the heart or other excitable tissue (e.g., neural targets) to restore or improve cardiac performance in a CHF patient, or to correct cardiac arrhythmia. For example, a detection of cardiac arrhythmia may trigger cardiac pacing or electric shock, or a detection of a WHF event may trigger electrostimulation therapy, such as a resynchronization therapy (CRT) to correct cardiac dyssynchrony in patients with heart failure.

An AMD can detect a cardiac event using heart sounds detected from a patient. For example, S1 and/or S2 may be used to detect cardiac arrhythmia such as supraventricular tachycardia or ventricular tachycardia. Pulmonary fluid accumulation in CHF patients may cause elevated ventricular filling pressure and diastolic dysfunction, resulting in pathologically louder S3. Forceful atrial contraction to overcome an abnormally stiff ventricle in a CHF patient may produce profound S4. Therefore, monitoring S3 or S4 may help determining patient diastolic dysfunction, detecting a WHF event, or assessing patient risk of developing future WHF.

Ambulatory heart sounds detection involves placing a heart sound sensor at an epicutaneous, subcutaneous, submuscular, intramuscular, or substernal location at or near the heart. The heart sound sensor, such as an accelerometer, may be included within an IMD for implantation, or associated with an implantable lead for epicardial or endocardial placement. S1 and S2 heart sounds generally have a frequency within a range of approximately 10-250 Hz. With a wide interpersonal variability and shifts secondary to technical equipment, S2 generally has a higher frequency than S1. For example, most of S1 power fall within approximately 10-50 Hz and most of S2 fall within approximately 20-07 Hz. Early diastole sound S3 produced by rapid filling of dilated ventricles, and late diastole sound S4 produced by contraction of the left atrium against a non-compliant left ventricle, when present, generally have lower intensity and lower frequencies.

Heart sound components (e.g., S1, S2, S3, or S4) are conventionally detected using a time-domain, amplitude-based approach which includes detecting a maximum signal amplitude or a variation thereof, such as peak heart sound signal power or root-mean-square (RMS) value of the heart sound signal, within a heart sound detection window. The timing of the maximum amplitude is then identified as the timing location of the heart sound component. However, often times multiple peaks can be present within the heart sound signal of an individual heart sound window, and the major peak (the one with the largest amplitude) may not always represent an actual heart sound component. As such, the time-domain, amplitude-based approach may sometimes mistakenly recognize a spurious peak as a target heart sound component. On the other hand, the time-domain, amplitude-based approach may be sensitive to electromagnetic or physiological noise or interferences. At a low signal-to-noise ratio (SNR), timing information of a heart sound component such as S1 or S2 may not be accurately determined. This may cause further errors in the detections of other heart sound components (e.g., S3 or S4) or heart sound-based cardiac time intervals that are measured in reference to the timings of S1 or S2 components, such as pre-ejection period (PEP, an interval between QRS onset and S1), a systolic timing interval (STI, an interval between QRS onset and S2), a left-ventricular ejection time (LVET, an interval between S1 and S2), or a diastolic timing interval (DTI, an interval between S2 and QRS onset of the next cardiac cycle). For cardiac event detections (e.g., WHF events) that depend on heart sound timings and/or cardiac time intervals, the detection performance may be reduced. For at least these reasons, the present inventors have recognized, among other things, that the time-domain, amplitude-based approach may not be a desirable identifier at least in certain occasions such as low SNR, and there remains an unmet need for more robust heart sound component recognition and more reliable cardiac event detection using such recognized heart sound component.

The present document discusses systems, devices, and methods for determine and tracking heart sound components based on spectral entropy of a heart sound signal. An exemplary medical-device system comprises a data receiver circuit to receive heart sound information, and a heart sound recognition circuit to generate a representative heart sound segment within a cardiac cycle, such as an ensemble average of a plurality of heart sound segments taken from multiple cardiac cycles. The heart sound recognition circuit can partition the representative heart sound segment into multiple heart sound data windows, calculate spectral entropy values respectively for each of the multiple heart sound data windows, and determine one or more heart sound components including an S2 component using the calculated spectral entropy values. The medical-device system may include a physiologic event detector to detect a cardiac event using the determined one or more heart sound components.

Example 1 is a medical-device system, comprising: a data receiver circuit configured to receive heart sound information; and a heart sound recognition circuit configured to: generate a representative heart sound segment within a cardiac cycle using at least a portion of the received heart sound information; partition the representative heart sound segment into multiple heart sound data windows; calculate spectral entropy values respectively for each of the multiple heart sound data windows; and determine one or more heart sound components including an S2 component using the calculated spectral entropy values.

In Example 2, the subject matter of Example 1 optionally includes the heart sound recognition circuit that can be configured to: partition the representative heart sound segment into the multiple heart sound data windows using a sliding time window; generate a spectral entropy time series by concatenating the calculated spectral entropy values in accordance with respective timings of the multiple heart sound data windows; and determine the one or more heart sound components including the S2 component using the spectral entropy time series.

In Example 3, the subject matter of any one or more of Examples 1-2 optionally includes the portion of the received heart sound information that can include a plurality of heart sound segments taken respectively from multiple cardiac cycles, wherein the heart sound recognition circuit is configured to: time-align the plurality of heart sound segments with respect to respective fiducial points; and generate the representative heart sound segment using an ensemble average of the time-aligned plurality of heart sound segments.

In Example 4, the subject matter of Example 3 optionally includes the data receiver circuit that can be configured to receive a cardiac electrical signal concurrently sensed with the heart sound information over the multiple cardiac cycles, wherein the respective fiducial points include ventricular activations for the multiple cardiac cycles of the concurrently sensed cardiac electrical signal.

In Example 5, the subject matter of any one or more of Examples 1-4 optionally includes the data receiver circuit that can be configured to receive information about instantaneous heart rates concurrently sensed with the heart sound information over multiple cardiac cycles, wherein the portion of the received heart sound information over the multiple cardiac cycles used for generating the representative heart sound segment corresponds to substantially identical instantaneous heart rates or within a pre-determined heart rate range.

In Example 6, the subject matter of any one or more of Examples 2-5 optionally includes the heart sound recognition circuit that can be configured to determine the S2 component based on a local minimum of a portion of the spectral entropy time series within an S2 detection window.

In Example 7, the subject matter of Example 6 optionally includes the data receiver circuit that can be configured to receive (i) a cardiac electrical signal and (ii) information about instantaneous heart rates, both of which are concurrently sensed with the heart sound information over multiple cardiac cycles, wherein the heart sound recognition circuit is configured to determine S2 detection window using ventricular activations on the cardiac electrical signal and the instantaneous heart rates.

In Example 8, the subject matter of any one or more of Examples 2-7 optionally includes the heart sound recognition circuit that can be configured to: generate, and store in a memory, one or more heart rate or rhythm dependent heart sound spectral entropy templates each including a spectral entropy time series of a heart sound at a corresponding heart rate or rhythm; and determine the one or more heart sound components further using the one or more heart rate or rhythm dependent heart sound spectral entropy templates.

In Example 9, the subject matter of Example 8 optionally includes the data receiver circuit that can be configured to receive information about an instantaneous heart rate or rhythm concurrently sensed with the heart sound information, wherein the heart sound recognition circuit is configured to: select one of the stored one or more heart rate or rhythm dependent heart sound spectral entropy templates with a corresponding heart rate or rhythm that matches the instantaneous heart rate or rhythm; and determine the one or more heart sound components using the selected stored heart rate or rhythm dependent heart sound spectral entropy template.

In Example 10, the subject matter of Example 9 optionally includes the heart sound recognition circuit that can be configured to: modify the spectral entropy time series of the representative heart sound segment with the selected stored heart rate or rhythm dependent heart sound spectral entropy template; and determine the one or more heart sound components using the modified spectral entropy time series of the representative heart sound segment.

In Example 11, the subject matter of Example 10 optionally includes, wherein to modify the spectral entropy time series of the representative heart sound segment, the heart sound recognition circuit can be configured to compute an average of (i) the spectral entropy time series of the representative heart sound segment and (ii) the spectral entropy time series in the selected stored heart rate or rhythm dependent heart sound spectral entropy template.

In Example 12, the subject matter of any one or more of Examples 10-11 optionally includes the heart sound recognition circuit that can be configured to update the selected stored heart rate or rhythm dependent heart sound spectral entropy template in the memory with the modified spectral entropy time series of the representative heart sound segment.

In Example 13, the subject matter of any one or more of Examples 1-12 optionally includes the heart sound recognition circuit that can be further configured to detect an S3 component or an S4 component from the representative heart sound segment based at least in part on timing information of the determined S2 component.

In Example 14, the subject matter of Example 13 optionally includes the heart sound recognition circuit that can be further configured to: determine a confidence of the determined S2 component; and detect the S3 component or the S4 component when the determined confidence exceeds a threshold.

In Example 15, the subject matter of any one or more of Examples 1-14 optionally includes a physiological event detector configured to a detect a cardiac event using the determined one or more heart sound components.

Example 16 is a method of recognizing a heart sound component, comprising: receiving heart sound (HS) information; generating a representative heart sound segment within a cardiac cycle using at least a portion of the received heart sound information; partitioning the representative heart sound segment into multiple heart sound data windows; calculating spectral entropy values respectively for each of the multiple heart sound data windows; and determining one or more heart sound components including an S2 component using the calculated spectral entropy values.

In Example 17, the subject matter of Example 16 optionally includes receiving information about instantaneous heart rates concurrently sensed with the heart sound information over multiple cardiac cycles, wherein the portion of the received heart sound information over the multiple cardiac cycles used for generating the representative heart sound segment corresponds to substantially identical instantaneous heart rates or within a pre-determined heart rate range.

In Example 18, the subject matter of Example 17 optionally includes determining the one or more heart sound components that can include: generating a spectral entropy time series by concatenating the calculated spectral entropy values in accordance with respective timings of the multiple heart sound data windows; and determining the one or more heart sound components including the S2 component based on a local minimum of a portion of the spectral entropy time series within an S2 detection window.

In Example 19, the subject matter of any one or more of Examples 17-18 optionally includes: generating and storing in memory one or more heart rate or rhythm dependent heart sound spectral entropy templates each including a spectral entropy time series of a heart sound at a particular heart rate or rhythm; and determine the one or more heart sound components further using the one or more heart rate or rhythm dependent heart sound spectral entropy templates.

In Example 20, the subject matter of Example 19 optionally includes: receiving information about an instantaneous heart rate or rhythm concurrently sensed with the heart sound information over multiple cardiac cycles; selecting one of the stored one or more heart rate or rhythm dependent heart sound spectral entropy templates with a corresponding heart rate or rhythm that matches the instantaneous heart rate or rhythm; and determine the one or more heart sound components using the selected stored heart rate or rhythm dependent heart sound spectral entropy template.

In Example 21, the subject matter of any one or more of Examples 19-20 optionally includes: generating a spectral entropy time series by concatenating the calculated spectral entropy values in accordance with respective timings of the multiple heart sound data windows; modifying the spectral entropy time series of the representative heart sound segment with the selected stored heart rate or rhythm dependent heart sound spectral entropy template; determine the one or more heart sound components using the modified spectral entropy time series of the representative heart sound segment; and updating the selected stored heart rate or rhythm dependent heart sound spectral entropy template in the memory with the modified spectral entropy time series of the representative heart sound segment.

In Example 22, the subject matter of any one or more of Examples 16-21 optionally includes detecting a cardiac event using the determined one or more heart sound components.

The spectral entropy-based heart sound recognition and tracking as described in this disclosure may improve the functionality of an ambulatory medical device, or a medical diagnostic system or device, that uses heart sound to detect a physiologic event, such as a cardiac arrhythmia episode or a WHF event or to assess cardiac performance, or to diagnose a cardiac condition. In contrast to conventional time-domain, amplitude-based heart sound recognition, the spectral entropy-based approach quantifies complexities (or non-uniformities) of power spectral magnitudes of a heart sound signal or a portion thereof such as within a cardiac cycle. A high spectral entropy indicates more uniformly distributed signal energy across a wide frequency range in the frequency domain, while a low spectral entropy indicates less uniformity in the signal energy distribution. A wideband signal (e.g., a white noise signal), characterized by signal energy spreading almost uniformly over a wide frequency range, and therefore has large spectral entropy. Conversely, a narrowband signal has most of its signal energy focused on a narrow frequency band and less uniformly distributed, and therefore a smaller spectral entropy. Certain heart sound components, such as S1 and S2, are narrowband signals. For example, S1 power generally falls within approximately 10-50 Hz, and S2 power generally falls within approximately 20-70 Hz. As such, S1 and S2 generally have lower spectral entropy values. The spectral entropy-based heart sound detection as described herein combines the advantages of frequency-domain spectral analysis and Shannon's entropy, both of which can be more robust to random noise and interferences from various sources than the time-domain, amplitude-based heart sound detection method. In particular, the spectral entropy-based approach is more immune to sporadic time-domain high-amplitude noise, which may more likely cause spurious detections when using the time-domain, amplitude-based heart sound detection method. With increased detection accuracy of heart sound components and particularly the timing information of such heart sound components, more reliable and efficient cardiac event detection (e.g., WHF or arrhythmias) and improved patient outcome can be achieved.

This Overview provides some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for tracking heart sound components, such as S1, S2, S3, or S4 components, based on spectral entropy of a heart sound signal. An exemplary medical-device system comprises a data receiver circuit to receive heart sound information, and a heart sound recognition circuit to generate a representative heart sound segment within a cardiac cycle, such as an ensemble average of a plurality of heart sound segments taken from multiple cardiac cycles. The heart sound recognition circuit can partition the representative heart sound segment into multiple heart sound data windows, calculate spectral entropy values respectively for each of the multiple heart sound data windows, and determine one or more heart sound components including an S2 component using the calculated spectral entropy values. A physiologic event detector can detect a cardiac event using the recognized one or more heart sound components.

Figure 1:
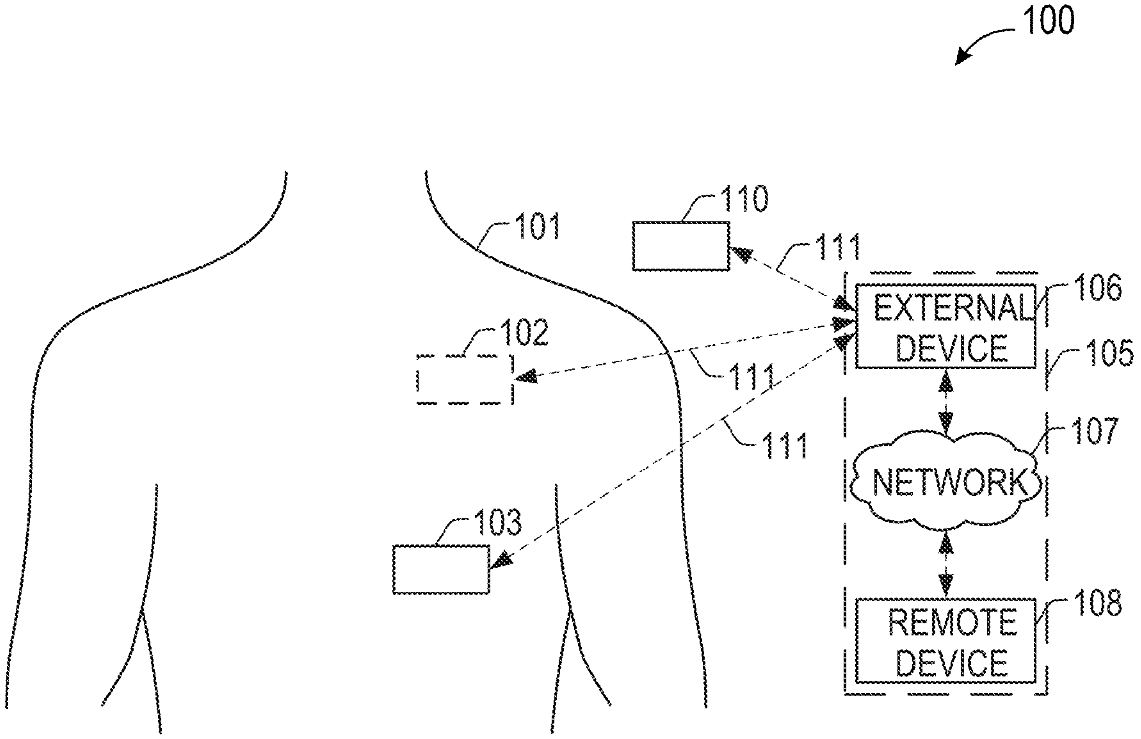
FIG. 1 illustrates generally an example of a patient management system and portions of an environment in which the system may operate.

FIG. 1 illustrates generally an example patient management system 100 and portions of an environment in which the patient management system 100 may operate. The patient management system 100 can perform a range of activities, including remote patient monitoring and diagnosis of a disease condition. Such activities can be performed proximal to a patient 101, such as in a patient home or office, through a centralized server, such as in a hospital, clinic, or physician office, or through a remote workstation, such as a secure wireless mobile computing device.

The patient management system 100 may include one or more ambulatory medical devices, an external system 105, and a communication link 111 providing for communication between the one or more ambulatory medical devices and the external system 105. The one or more ambulatory medical devices may include an implantable medical device (IMD) 102, a wearable medical device (WMD) 103, or one or more other implantable, leadless, subcutaneous, external, wearable, or ambulatory medical devices configured to monitor, sense, or detect information from, determine physiologic information about, or provide one or more therapies to treat various conditions of the patient 101, such as one or more cardiac or non-cardiac conditions (e.g., dehydration, sleep disordered breathing, etc.).

In an example, the IMD 102 may include one or more traditional cardiac rhythm management devices implanted in a chest of a patient, having a lead system including one or more transvenous, subcutaneous, or non-invasive leads or catheters to position one or more electrodes or other sensors (e.g., a heart sound sensor) in, on, or about a heart or one or more other position in a thorax, abdomen, or neck of the patient 101. In another example, the IMD 102 may include a monitor implanted, for example, subcutaneously in the chest of patient 101, the IMD 102 including a housing containing circuitry and, in certain examples, one or more sensors, such as a temperature sensor, etc.

The IMD 102 may include an assessment circuit configured to detect or determine specific physiologic information of the patient 101, or to determine one or more conditions or provide information or an alert to a user, such as the patient 101 (e.g., a patient), a clinician, or one or more other caregivers or processes. In an example, the IMD 102 can be an implantable cardiac monitor (ICM) configured to collected cardiac information, optionally along with other physiological information, from the patient. The IMD 102 can alternatively or additionally be configured as a therapeutic device configured to treat one or more medical conditions of the patient 101. The therapy can be delivered to the patient 101 via the lead system and associated electrodes or using one or more other delivery mechanisms. The therapy may include delivery of one or more drugs to the patient 101, such as using the IMD 102 or one or more of the other ambulatory medical devices, etc. In some examples, therapy may include cardiac resynchronization therapy for rectifying dyssynchrony and improving cardiac function in heart failure patients. In other examples, the IMD 102 may include a drug delivery system, such as a drug infusion pump to deliver drugs to the patient for managing arrhythmias or complications from arrhythmias, hypertension, or one or more other physiologic conditions. In other examples, the ID 102 may include one or more electrodes configured to stimulate the nervous system of the patient or to provide stimulation to the muscles of the patient airway, etc.

The WMD 103 may include one or more wearable or external medical sensors or devices (e.g., automatic external defibrillators (AEDs), Holter monitors, patch-based devices, smart watches, smart accessories, wrist- or finger-worn medical devices, such as a finger-based photoplethysmography sensor, etc.).

In an example, the IMD 102 or the WMD 103 may include or be coupled to an implantable or wearable sensor to sense a heart sound signal, and include a heart sound recognition circuit to recognize one or more heart sound components such as S1, S2, S3, or S4 based on a spectral entropy time series derived from the sensed heart sound signal. Also included in the IMD 102 or the WMD 103 is a heart sound-based event detector circuit that can detect a physiologic event (e.g., a cardiac arrhythmia episode, or a worsening heart failure (WHF) event) based at least on a heart sound metric of the detected one or more heart sound component. Examples of such heart sound metric may include an amplitude, or timing of the heart sound component within a cardiac cycle relative to a fiducial point. In some examples, at least a portion of the heart sound recognition circuit and/or the heart sound-based event detector circuit may be implemented in and executed by the external system 105.

The external system 105 may include a dedicated hardware/software system, such as a programmer, a remote server-based patient management system, or alternatively a system defined predominantly by software running on a standard personal computer. The external system 105 can manage the patient 101 through the IMD 102 or one or more other ambulatory medical devices connected to the external system 105 via a communication link 111. In other examples, the IMD 102 can be connected to the WMD 103, or the WMD 103 can be connected to the external system 105, via the communication link 111. This may include, for example, programming the IMD 102 to perform one or more of acquiring physiological data, performing at least one self-diagnostic test (such as for a device operational status), analyzing the physiological data, or optionally delivering or adjusting a therapy for the patient 101. Additionally, the external system 105 can send information to, or receive information from, the IMD 102 or the WMD 103 via the communication link 111. Examples of the information may include real-time or stored physiological data from the patient 101, diagnostic data, such as detection of patient hydration status, hospitalizations, responses to therapies delivered to the patient 101, or device operational status of the IMD 102 or the WMD 103 (e.g., battery status, lead impedance, etc.). The communication link 111 can be an inductive telemetry link, a capacitive telemetry link, or a radio-frequency (RF) telemetry link, or wireless telemetry based on, for example, "strong" Bluetooth or IEEE 802.11 wireless fidelity "Wi-Fi" interfacing standards. Other configurations and combinations of patient data source interfacing are possible.

The external system 105 may include an external device 106 in proximity of the one or more ambulatory medical devices, and a remote device 108 in a location relatively distant from the one or more ambulatory medical devices, in communication with the external device 106 via a communication network 107. Examples of the external device 106 may include a medical device programmer. The remote device 108 can be configured to evaluate collected patient or patient information and provide alert notifications, among other possible functions. In an example, the remote device 108 may include a centralized server acting as a central hub for collected data storage and analysis. The server can be configured as a uni-, multi-, or distributed computing and processing system. The remote device 108 can receive data from multiple patients. The data can be collected by the one or more ambulatory medical devices, among other data acquisition sensors or devices associated with the patient 101. The server may include a memory device to store the data in a patient database. The server may include an alert analyzer circuit to evaluate the collected data to determine if specific alert condition is satisfied. Satisfaction of the alert condition may trigger a generation of alert notifications, such to be provided by one or more human-perceptible user interfaces. In some examples, the alert conditions may alternatively or additionally be evaluated by the one or more ambulatory medical devices, such as the implantable medical device. By way of example, alert notifications may include a Web page update, phone or pager call, E-mail, SMS, text or "Instant" message, as well as a message to the patient and a simultaneous direct notification to emergency services and to the clinician. Other alert notifications are possible. The server may include an alert prioritizer circuit configured to prioritize the alert notifications. For example, an alert of a detected physiologic event can be prioritized using a similarity metric between the physiological data associated with the detected physiologic event to physiological data associated with the historical alerts.

The remote device 108 may additionally include one or more locally configured clients or remote clients securely connected over the communication network 107 to the server. Examples of the clients may include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning. In addition to generating alert notifications, the remote device 108, including the server and the interconnected clients, may also execute a follow-up scheme by sending follow-up requests to the one or more ambulatory medical devices, or by sending a message or other communication to the patient 101 (e.g., the patient), clinician or authorized third party as a compliance notification.

The communication network 107 can provide wired or wireless interconnectivity. In an example, the communication network 107 can be based on the Transmission Control Protocol/Internet Protocol (TCP/IP) network communication specification, although other types or combinations of networking implementations are possible. Similarly, other network topologies and arrangements are possible.

One or more of the external device 106 or the remote device 108 can output the detected physiologic events to a system user, such as the patient or a clinician, or to a process including, for example, an instance of a computer program executable in a microprocessor. In an example, the process may include an automated generation of recommendations for anti-arrhythmic therapy, or a recommendation for further diagnostic test or treatment. In an example, the external device 106 or the remote device 108 may include a respective display unit for displaying the physiologic or functional signals, or alerts, alarms, emergency calls, or other forms of warnings to signal the detection of arrhythmias. In some examples, the external system 105 may include an external data processor configured to analyze the physiologic or functional signals received by the one or more ambulatory medical devices, and to confirm or reject the detection of arrhythmias. Computationally intensive algorithms, such as machine-learning algorithms, can be implemented in the external data processor to process the data retrospectively to detect cardia arrhythmias.

Portions of the one or more ambulatory medical devices or the external system 105 can be implemented using hardware, software, firmware, or combinations thereof. Portions of the one or more ambulatory medical devices or the external system 105 can be implemented using an application-specific circuit that can be constructed or configured to perform one or more functions or can be implemented using a general-purpose circuit that can be programmed or otherwise configured to perform one or more functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. "Sensors" may include electronic circuits configured to receive information and provide an electronic output representative of such received information.

The therapy device 110 can be configured to send information to or receive information from one or more of the ambulatory medical devices or the external system 105 using the communication link 111. In an example, the one or more ambulatory medical devices, the external device 106, or the remote device 108 can be configured to control one or more parameters of the therapy device 110. The external system 105 can allow for programming the one or more ambulatory medical devices and can receives information about one or more signals acquired by the one or more ambulatory medical devices, such as can be received via a communication link 111. The external system 105 may include a local external implantable medical device programmer. The external system 105 may include a remote patient management system that can monitor patient status or adjust one or more therapies such as from a remote location.

Figure 2:
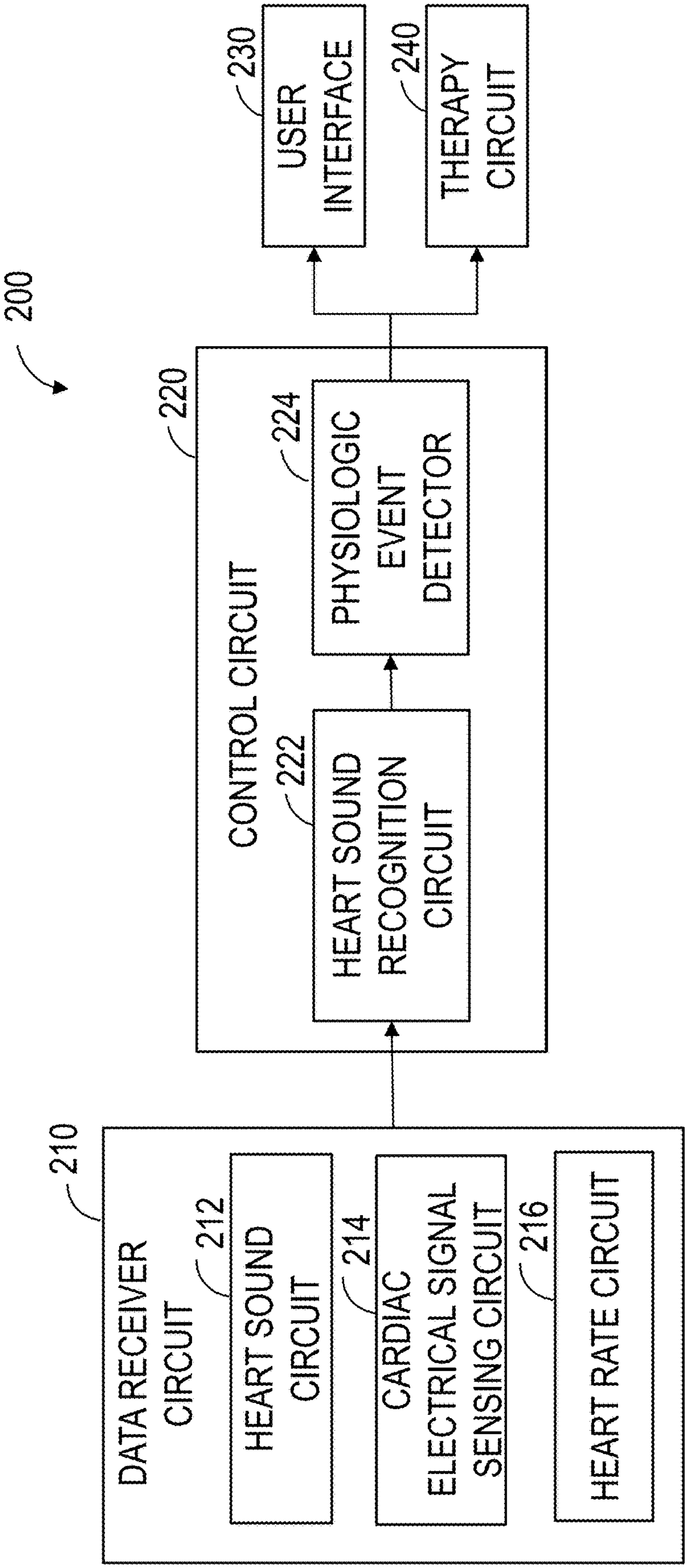
FIG. 2 illustrates generally an example of a heart sound-based physiologic event detection system configured to recognize a heart sound component and use recognized heart sound component to detect a physiologic event.

FIG. 2 illustrates generally an example of a heart sound-based physiologic event detection system 200 that can recognize and track a heart sound component, and use the recognized heart sound component to detect a physiologic event, such as a cardiac arrhythmia episode or a worsening heart failure (WHF) event. The physiologic event detection system 200 may include one or more of a data receiver circuit 210, a control circuit 220, a user interface 230, and a therapy circuit 240. At least a portion of the physiologic event detection system 200 may be implemented in the IMD 102, the WMD 103, or the external system 105 such as one or more of the external device 106 or the remote device 108.

The data receiver circuit 210 may receive physiologic information from a patient. In an example, the data receiver circuit 210 may include a sense amplifier circuit configured to sense a physiologic signal from a patient via a physiologic sensor, such as an implantable, wearable, or otherwise ambulatory sensor or electrodes associated with the patient. The sensor may be incorporated into, or otherwise associated with an ambulatory device such as the IMD 102 or the WMD 103. In some examples, the physiologic signals sensed from a patient may be stored in a storage device, such as an electronic medical record (EMR) system. The data receiver circuit 210 may receive the physiologic signal from the storage device, such as in response to a user command or a triggering event. By way of example and not limitation and as illustrated in FIG. 2, the data receiver circuit 210 may include a heart sound sensing circuit 212, a cardiac electrical signal sensing circuit 214, and a heart rate circuit 216. The heart sound sensing circuit 212 can receive heart sound information, such as a heart sound signal sensed from the patient. In an example, the heart sound sensing circuit 212 may be coupled to a heart sound sensor to sense a body motion/vibration signal indicative of cardiac vibration, which is correlated to or indicative of heart sounds. The heart sound sensor may take the form of an accelerometer, an acoustic sensor, a microphone, a piezo-based sensor, or other vibrational or acoustic sensors. The accelerometer can be a one-axis, a two-axis, or a three-axis accelerometer. Examples of the accelerometer may include flexible piezoelectric crystal (e.g., quartz) accelerometer or capacitive accelerometer, fabricated using micro electro-mechanical systems (MEMS) technology. The heart sound sensor may be included in the IMD 102 or the WMD 103, or disposed on a lead such as a part of the lead system associated with the IMD 102 or the WMD 103. In an example, an accelerometer (or other sensor types) may sense an epicardial or endocardial acceleration (EA) signal from a portion of a heart, such as on an endocardial or epicardial surface of one of a left ventricle, a right ventricle, a left atrium, or a right atrium. The EA signal may contain components corresponding to various heart sound components such as one or more of S1, S2, S3, or S4.

The cardiac electrical signal sensing circuit 214 can sense a cardiac electrical signal. Examples of the cardiac electrical signal may include surface electrocardiography (ECG) sensed from electrodes placed on the body surface, subcutaneous ECG sensed from electrodes placed under the skin, intracardiac electrogram (EGM) sensed from the one or more implantable electrodes. The sensing electrodes can be included in or communicatively coupled to the IMD 102 or the WMD 103. The heart rate circuit 216 can detect heart rate of the patient, such as from the signal sensed by the cardiac electrical signal sensing circuit 214. Alternatively, the heart rate (or pulse rate) can be detected from a cardiac mechanical signal. As to be discussed further below, one or more of the cardiac electrical signal or the heart rate information may be used by the control circuit to construct a representative heart sound segment from which a spectral entropy time series can be derived.

In some examples, the data receiver circuit 210 may receive other physiological or functional signals including, for example, physical activity signal, posture signal, a thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal, physiologic response to activity, apnea hypopnea index, one or more respiration signals such as a respiratory rate signal or a tidal volume signal, brain natriuretic peptide (BNP), blood panel, sodium and potassium levels, glucose level and other biomarkers and bio-chemical markers, among others.

The control circuit 220 can recognize and track a heart sound component, and detect a physiologic event based at least one the heart sound component. The control circuit 220 be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein.

The control circuit 220 may include circuit sets comprising one or more other circuits or sub-circuits, such as a heart sound recognition circuit 222 and a physiologic event detector 224. These circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The heart sound recognition circuit 222 can preprocess the heart sound signal received from the heart sound sensing circuit 212. In an example, the heart sound recognition circuit 222 may include a filter or a filter bank to remove or attenuate one or more of low-frequency signal baseline drift, high frequency noise, or other unwanted frequency contents. In an example, the heart sound segment may be band-pass filtered to a frequency range of approximately 5-90 Hz, or approximately 9-90 Hz. In an example, the filter may include a double or higher-order differentiator configured to calculate a double or higher-order differentiation of the heart sound signal.

Figure 3A:
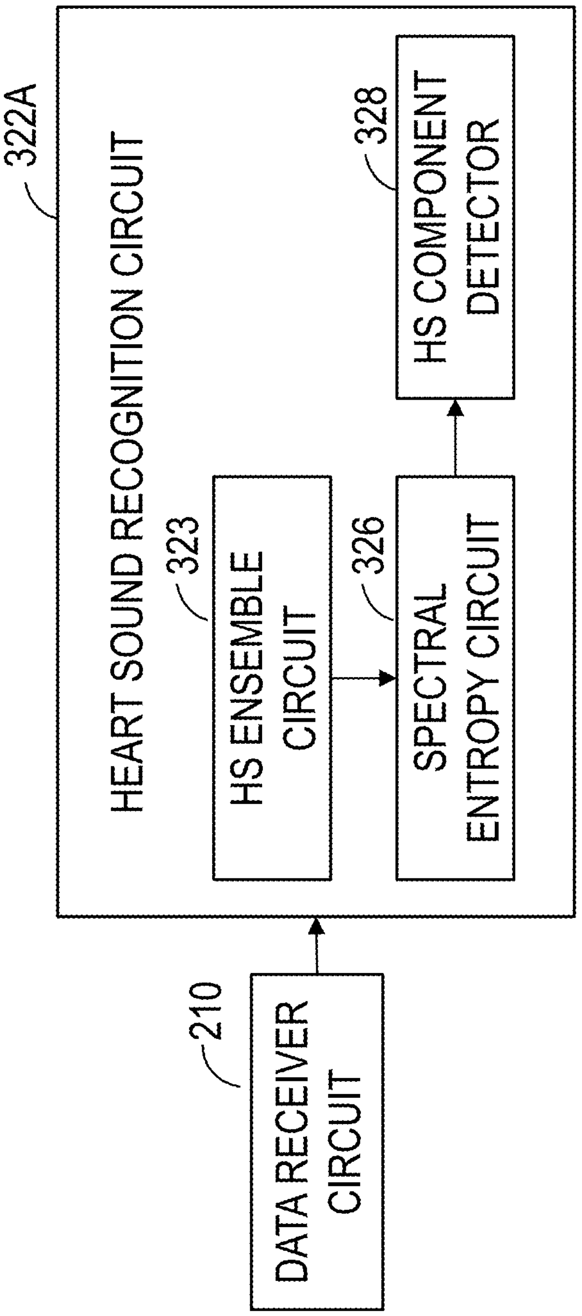
FIG. 3A-3B illustrate examples of a heart sound recognition circuit that recognize heart sound components from a spectral entropy time series.
Figure 3B:
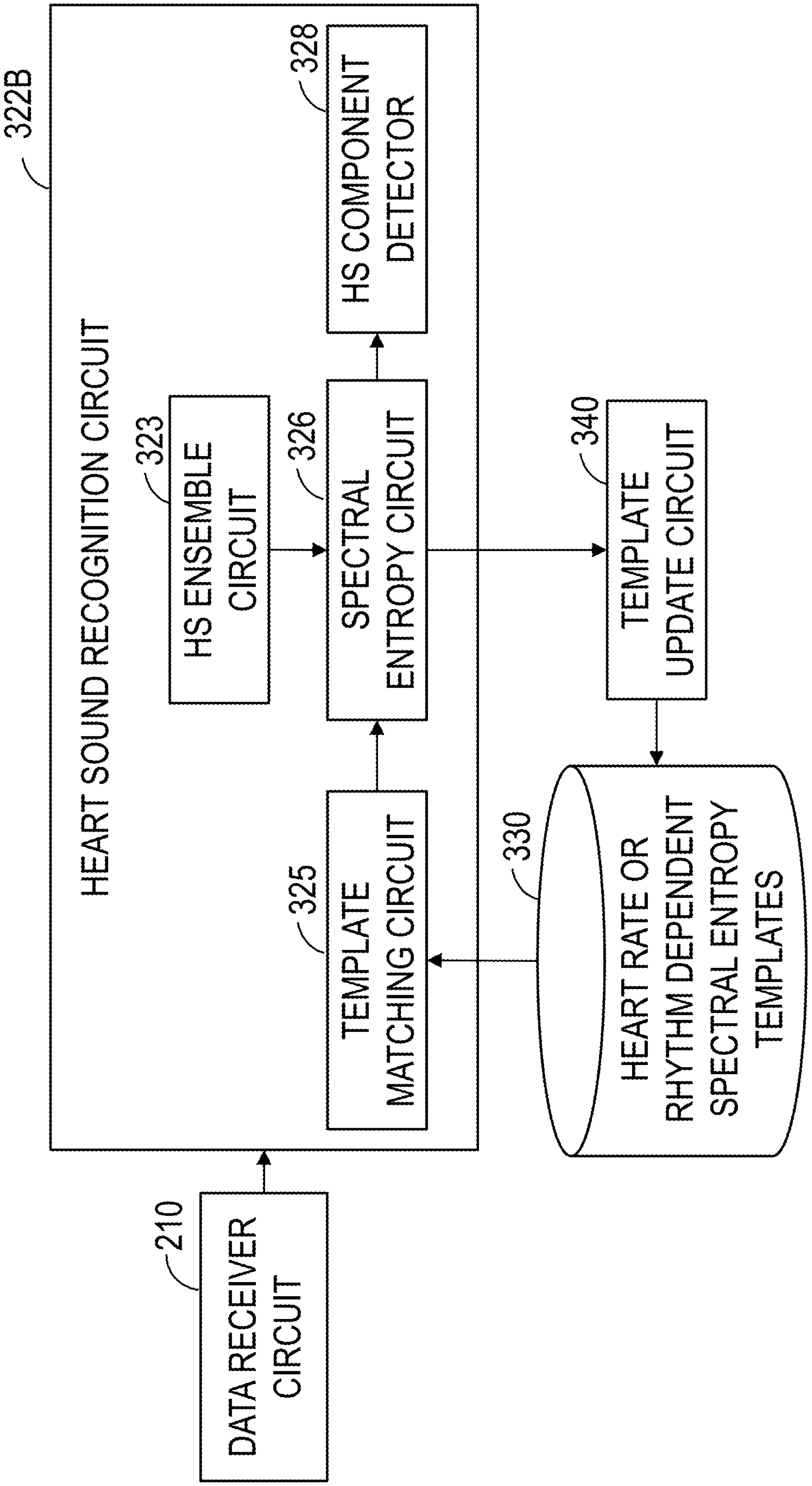

The heart sound recognition circuit 222 may recognize a heart sound component from the preprocessed heart sound signal, optionally further using the cardiac electrical signal and the heart rate information provided by the cardiac electrical signal sensing circuit 214 and the heart rate circuit 216, respectively. The heart sound component can be recognized using a spectral entropy time series of a representative segment of the heart sound signal. FIGS. 3A-3B illustrates, by way of example and not limitation, embodiments of the heart sound recognition circuit 222, such as heart sound recognition circuits 322A and 322B as shown in FIGS. 3A and 3B, respectively. As shown in FIG. 3A, the heart sound recognition circuits 322A includes a heart sound ensemble circuit 323, a spectral entropy circuit 326, and a heart sound component detector 328. The heart sound ensemble circuit 323 can generate a heart sound ensemble comprising a plurality of segments of the received heart sound signal, such as heart sound segments within respective multiple cardiac cycles. In an example, the heart sound ensemble circuit 323 can use the cardiac electrical signals (received from the cardiac electrical signal sensing circuit 214) concurrently sensed with the heart sound signal. The heart sound ensemble circuit 323 may detect cardiac cycles as time intervals between two consecutive cardiac activations (e.g., R waves or QRS complexes) on the ECG or intracardiac EGM signal. The heart sound ensemble circuit 323 may align the plurality of heart sound segments with respect to respective fiducial points for the multiple cardiac cycles. The fiducial points may include, for example, ventricular activations (e.g., R waves) in the multiple cardiac cycles of the ECG or EGM signal.

In some examples, the heart sound ensemble circuit 323 may screen the received heart sound signal, such as heart sound segments in multiple cardiac cycles, and select a subset of the heart sound segments that satisfy a specified criterion to form the heart sound ensemble. The screening criterion may include one or more of patient activity level, heart rate, respiration rate, or time of a day, among other conditions. In an example, the heart sound ensemble circuit 323 can select a subset of the heart sound segments with the corresponding heart rates or cycle lengths falling within a specified range, such as substantially the same cycle length within a margin of +/−100 milliseconds, or substantially the same heart rate within a margin of +/−5 beats per minute. In another example, the heart sound ensemble circuit 323 can select a subset of the heart sound segments with the corresponding physical activity levels falling within a specified range, such as substantially the same physical activity level within a specified margin, or a subset of heart sound segments with the corresponding respiratory rates falling within a specified range, such as substantially the same respiratory rate within a specified margin. In yet another example, the heart sound signal may be sensed during a specified time period of a day. The heart sound ensemble circuit 323 can select a subset of the heart sound segments that are sensed during substantially the same time period of a day within a specified margin.

The heart sound ensemble circuit 323 may align the selected subset of the heart sound signal segments form the heart sound ensemble. The alignment can be with respect to the R waves on an ECG signal concurrently sensed with the heart sound within corresponding cardiac cycles. The heart sound ensemble circuit 323 may generate a representative heart sound segment within a cardiac cycle using the aligned selected subset of the heart sound signal segments. In an example, the representative heart sound segment can be an ensemble average of the aligned selected subset of the heart sound signal segments.

The spectral entropy circuit 326 can generate a spectral entropy time series using the representative heart sound segment. The spectral entropy quantifies complexities (or non-uniformities) of power spectral magnitudes of a heart sound segment within a cardiac cycle. A high spectral entropy indicates more uniformly distributed signal energy more uniformly distributed signal energy across a wide frequency range in the frequency domain, while a low spectral entropy indicates less uniformity in the signal energy distribution. A wideband signal has its signal energy spreading almost uniformly over a wide frequency range, and therefore has a large spectral entropy. Conversely, a narrowband signal has most of its signal energy focused on a narrow frequency band, and therefore a smaller spectral entropy. To determine the spectral entropy time series, the spectral entropy circuit 326 can apply a sliding time window to the representative (e.g., ensemble-averaged) heart sound segment, and generate multiple heart sound data windows, calculate respective spectral entropy values for each of the multiple heart sound data windows, and concatenate the calculated spectral entropy values at respective timings of the heart sound data windows to form a spectral entropy time series.

The heart sound component detector 328 can recognize one or more heart sound components from the spectral entropy time series. Certain heart sound components, such as S1 and S2, are narrowband signals. For example, S1 power generally falls within approximately 10-50 Hz, and S2 power generally falls within approximately 20-70 Hz. Such heart sound components generally have lower respective spectral entropy values than other portions of the heart sound signal. The heart sound component detector 328 can recognize S1 based on a local minimum of a portion of the spectral entropy time series within an S1 detection window. Similarly, the heart sound component detector 328 can recognize S2 based on a local minimum of a portion of the spectral entropy time series within an S2 detection window. The S1 and S2 detection windows can have user-programmable locations (e.g., the beginning or the end of the detection window) and window lengths. In an example, an S1 detection window may begin at 50 milliseconds (msec) following a detected R wave on an ECG signal and have a duration of 300 msec. An S2 detection window can begin at specified offset following a detected R wave or S1 heart sound. In some examples, locations and lengths of S1 and S2 detection windows can be determined using spectral entropy time series of heart sound signals collected from a patient population. In some examples, the heart sound component detector 328 can compare the spectral entropy time series to a predetermined threshold, and detect local minimum from the portions of the spectral entropy time series below that predetermined threshold (which may be corresponding to S1 and/S2). S1 and S2 can be differentially recognized based on respective timings of the detected local minima. Examples of the generating a spectral entropy time series and detecting a heart sound component using the same are discussed below with reference to FIGS. 4 and 5.

The heart sound component detector 328 can detect other heart sound components such as S3 or S4 components from the spectral entropy time series using the methods as described above for detecting S1 and/or S2 components. Alternatively or additionally, the heart sound component detector 328 can detect S3 or S4 component based on the detected S1 and/or S2 components. For example, the heart sound component detector 328 can detect S3 within an S3 detection window using the spectral entropy time series or a heart sound energy signal. The S3 detection window can be defined based on the R-wave timing or the timing of the detected S2. In an example, the S3 detection window may begin at the S2 timing, or a specified offset following the detected S2 (e.g., approximately 50-125 msec following the S2 timing). The S3 detection window may have a duration of approximately 125 msec. In some examples, the offset or the S3 window duration may be a function of a physiological variable such as a heart rate. For example, the offset may be inversely proportional to the heart rate, such that the S3 detection window may start at a smaller offset following the S2 at a higher heart rate. In another example, the heart sound component detector 328 can detect S4 using the spectral entropy time series or a heart sound energy signal within an S4 detection window. Because S4 generally occurs temporally following S3 and prior to S1 of the next cardiac cycle, the S4 detection window can be defined to begin at S3 or at a specified offset following S3, and ends at R wave or S1 heart sound in the next cardiac cycle.

In some examples, the heart sound component detector 328 can determine a confidence of the recognition of heart sound component, such as a confidence of S1 timing or S2 timing (temporal locations with respect to a fiducial point such as the R wave in the same cardiac cycle). In an example, the confidence can be determined based on the spectral entropy amplitude in the S1 detection window or in the S2 detection window relative to a spectral entropy floor, such as spectral entropy values of the heart sound signal portions outside the S1 detection window and the S2 detection window. A high confidence of S1 or S2 recognition can be determined if the spectral entropy amplitude in the S1 detection window or in the S2 detection window is below the spectral entropy floor beyond a predetermined margin. Conversely, a low confidence of S1 or S2 recognition can be determined if the spectral entropy amplitude in the S1 detection window or in the S2 detection window is within the predetermined margin of the spectral entropy floor. In some cases, aberrant conductions or arrhythmias (e.g., bigeminy and trigeminy rhythms) may result in high variability in heart sounds even at substantially the same heart rate due to a delay impact of a previous beat on hemodynamics. Accordingly, a lower confidence of S1 or S2 timings can be determined when such arrhythmia or aberrant conductions are detected. In some examples, timings of S1 or S2 can be tracked over time, and a consistent pattern of spectral entropy troughs over time can be indicative of a high confidence of S1 or S2, while a less consistent pattern may suggest a low confidence. The heart sound component detector 328 may adjust the detection of other heart sound components (e.g., S3 or S4) based on the confidence of S1 or S2 detection. For example, the heart sound component detector 328 may detect S3 or S4 in the same cardiac cycle (as the detected S2) only when the confidence of S2 timing exceeds a threshold.

FIG. 3B illustrates a heart sound recognition circuit 322B that also includes the heart sound ensemble circuit 323, the spectral entropy circuit 326, and the heart sound component detector 328. The heart sound recognition circuit 322B may additionally include a template matching circuit 325 communicatively coupled to a storage device (e.g., a memory) that stores a database 330 of one or more heart rate or rhythm dependent heart sound spectral entropy templates. In an example, heart rate-dependent heart sound spectral entropy templates can be generated using heart sounds data from a patient population, such as a plurality of patients with similar medical conditions or demographics. Each of said templates may include one or more of a spectral entropy time series $SE_T$, spectral entropy values of heart sound components such as S1 and S2, or S1 and S2 timings with respect of a fiducial point such as R wave, all of which can be determined at a specific heart rate or heart rate range. The heart rate-dependent heart sound spectral entropy templates can be constructed as a lookup table or an association map with an established correspondence between heart rates (or heart rate ranges) and corresponding template information (e.g., spectral entropy time series, S1 and S2 timings, etc.). The template matching circuit 325 can receive from the heart rate circuit 216 information about instantaneous heart rates concurrently sensed with the heart sound information over multiple cardiac cycles, query the database 330 to identify, from the stored heart rate-dependent HS spectral entropy templates, a heart rate-matched template with a corresponding heart rate or heart rate range that matches the concurrently sensed instantaneous heart rate. The heat rate-matched template may include one or more of a heart rate-matched spectral entropy time series $SE_T$(HR), heart rate-matched spectral entropy values of heart sound components such as S1 and S2, or heart rate-matched S1 and S2 timings.

The heart sound component detector 328 can detect heart sound components using the heart rate-matched template. In an example, the heart sound component detector 328 may detect heart sound components using only the rate-matched template. For example, instead of using the representative heart sound segment (produced by the heart sound ensemble circuit 323) to recognize S1 or S2, the heart sound component detector 328 can recognize S1 or S2 (or retrieve information thereabout) directly from the heart rate-matched template. If the heart rate-matched template stores heart rate-matched S1 or S2 timings, said timings can be retrieved and used as approximates of S1 or S2 timings. Such approximation by using the previously stored S1 and S2 timing information can reduce the computation time and improves the efficiency of S1 or S2 tracking. In some examples, the heart sound component detector 328 may additionally detect other heart sound components such as S3 from the representative heart sound segment, based at least on the S1 or S2 timings derived or retrieved from the heart rate-matched template.

In another example, the spectral entropy circuit 326 can apply a sliding time window to the representative heart sound segment to generate multiple heart sound data windows, and generate a spectral entropy time series SE, as similarly described above with reference to FIG. 3A. The spectral entropy circuit 326 can then modify the spectral entropy time series SE by the heart rate-matched spectral entropy time series $SE_T$(HR) stored in the heart rate-matched spectral entropy template. An example of the modified SE, SE', may include an average of (i) the spectral entropy time series SE of the representative heart sound segment, and (ii) the heart rate-matched spectral entropy time series $SE_T$(HR) stored in the heart rate-matched spectral entropy template. The heart sound component detector 328 can then detect heart sound components from the modified spectral entropy time series SE' using the technique as described above with reference to FIG. 3A.

A template update circuit 340 can update the heart rate-matched spectral entropy template in the database 330 with the modified spectral entropy time series SE'. For example, the heart rate-matched spectral entropy time series $SE_T$(HR) (which is part of the heart rate-matched spectral entropy template stored in the database 330) can be replaced with the modified spectral entropy time series SE'. The updated spectral entropy template can be stored in the database 330 for future use.

In some examples, the database 330 may store one or more heart rhythm-dependent heart sound spectral entropy templates. Unlike the heart rate-dependent heart sound spectral entropy templates which are generated using heart sounds data (e.g., from a patient population with similar medical conditions or demographics) at a specific heart rate or heart rate range, the heart rhythm-dependent heart sound spectral entropy templates can be generated using heart sounds data from a patient population when the patients experience a particular type of cardiac rhythm, such as atrial fibrillation, atrial flutter, premature ventricular contractions, bigeminy, trigeminy, ventricular arrhythmia, etc. The heart rhythm-dependent heart sound spectral entropy templates can be constructed as a lookup table or an association map. Similar to the heart rate-based template matching as described above with respect to FIG. 3B, in an example, the template matching circuit 325 can receive from the data receiver circuit 210 information about cardiac rhythm during which the heart sound data is collected, or determine the cardiac rhythm using the cardiac signals, received from the cardiac electrical signal sensing circuit 214, that are concurrently sensed with the heart sound information. The template matching circuit 325 can query the database 330 to identify, from the stored heart rhythm-dependent HS spectral entropy templates, a heart rhythm-matched template with a corresponding heart rhythm matching the type of the rhythm of the concurrently sensed cardiac signal. The heart sound component detector 328 can then detect heart sound components using the heart rhythm-matched template in a similar way as described above with respect to the use of heart rate-matched template.

Referring back to FIG. 2, the physiologic event detector 224 can detect a physiologic event using one or more of the detected heart sound components. In some examples, the physiologic event detector 224 may generate a heart sound metric using the detected heart sound components, and detect the physiologic event using the heart sound metrics, optionally along with other physiologic information acquired from the patient. Examples of the heart sound metric may include an intensity (e.g., amplitude or signal energy under the curve) of a heart sound component, or one or more heart sound-based cardiac timing intervals, such as a pre-ejection period (PEP) such as measured between the onset of the QRS to the S1 heart sound, a systolic timing interval (STI) such as measured between the onset of the QRS complex on the ECG to the S2 heart sound, a left-ventricular ejection time (LVET) such as measured as an interval between S1 and S2 heart sounds, or a diastolic timing interval (DTI) such as measured between the S2 heart sound and the onset of the subsequent QRS complex on the ECG, among others. These heart sound-based cardiac timing intervals may be correlated with cardiac contractility or cardiac diastolic function of the heart. The heart sound metrics may further include PEP/LVET ratio, STI/DTI ratio, STI/cycle length (CL) ratio, or DTI/CL ratio, or other composite metrics.

In an example, the physiologic event detector 224 may track a heart sound component over time and generate a heart sound trend, such as an S1 amplitude trend, an S2 amplitude trend, an S1 timing trend, an S2 timing trend, or a trend of heart sound-based cardiac timing intervals (e.g., a PEP trend, an STI trend, an LVET trend, a DEI trend, etc.). Examples of tracking a heart sound component over time are described further below with reference to FIGS. 6A-6D. Based on the heart sound trend, the physiologic event detector 224 can generate a cardiac function indicator indicating myocardial contractility, cardiac synchrony, and cardiac hemodynamics. In an example, the physiologic event detector 224 may detect a cardiac arrhythmia episode, or distinguish between different arrhythmias (e.g., atrial tachyarrhythmia, supraventricular tachyarrhythmia, or ventricular tachyarrhythmia) using one or more of S1 intensity, S2 intensity, or a measure of STI. For example, a reduction in S1 intensity may be indicative of reduced cardiac contractility, and a reduction in S2 intensity may be indicative of reduced cardiac output, both of which may be used to detect cardiac arrhythmias and deterioration of cardiac hemodynamics during arrhythmia. In another example, the heart sound metrics, such as S3 intensity, may be used to detect WHF. An increase in S3 intensity indicates reduced ventricular compliance and deteriorating diastolic function, signifying occurrence of WHF. Additionally or alternatively, a reduction in S1 intensity, or a reduction in STI may indicate poor cardiac contractility or reduced electromechanical coupling, which signifies occurrence of WHF. An example of detecting WHF based on heart sound components recognized and tracked using the spectral entropy-based approach is described further below with reference to FIG. 7. The physiologic event detector 224 may additionally or alternatively detect respiratory, renal, neurological, among other medical conditions, based on the heart sound metrics.

The user interface 230 may include an input unit and an output unit. In an example, at least a portion of the user interface 230 may be implemented in the external system 105. The input unit may receive user input for programming the data receiver circuit 210 and the control circuit 220, such as parameters for sensing the heart sound signal, computing spectral entropy, detecting a heart sound component, generating a heart sound metric, or detecting a physiologic event. The input unit may include a keyboard, on-screen keyboard, mouse, trackball, touchpad, touch-screen, or other pointing or navigating devices. The output unit may include a display for displaying the sensed heart sound signal, the representative heart sound segments, the spectral entropy time series, the heart sound metrics, information about the detected physiologic events, and any intermediate measurements or computations, among others. The output unit may also present to a user, such as via a display unit, the therapy titration protocol and recommended therapy, including a change of parameters in the therapy provided by an implanted device, the prescription to get a device implanted, the initiation or change in a drug therapy, or other treatment options of a patient. The output unit may include a printer for printing hard copies of information that may be displayed on a display unit. The signals and information may be presented in a table, a chart, a diagram, or any other types of textual, tabular, or graphical presentation formats. The presentation of the output information may include audio or other media format. In an example, the output unit may generate alerts, alarms, emergency calls, or other forms of warnings to signal the system user about the detected medical events.

The therapy circuit 240 may be configured to deliver a therapy to the patient, such as in response to the detected physiologic event. The therapy may be preventive or therapeutic in nature such as to modify, restore, or improve patient neural, cardiac, or respiratory functions. Examples of the therapy may include electrostimulation therapy delivered to the heart, a nerve tissue, other target tissues, a cardioversion therapy, a defibrillation therapy, or drug therapy including delivering drug to the patient. In some examples, the therapy circuit 240 may modify an existing therapy, such as adjust a stimulation parameter or drug dosage.

Figure 4:
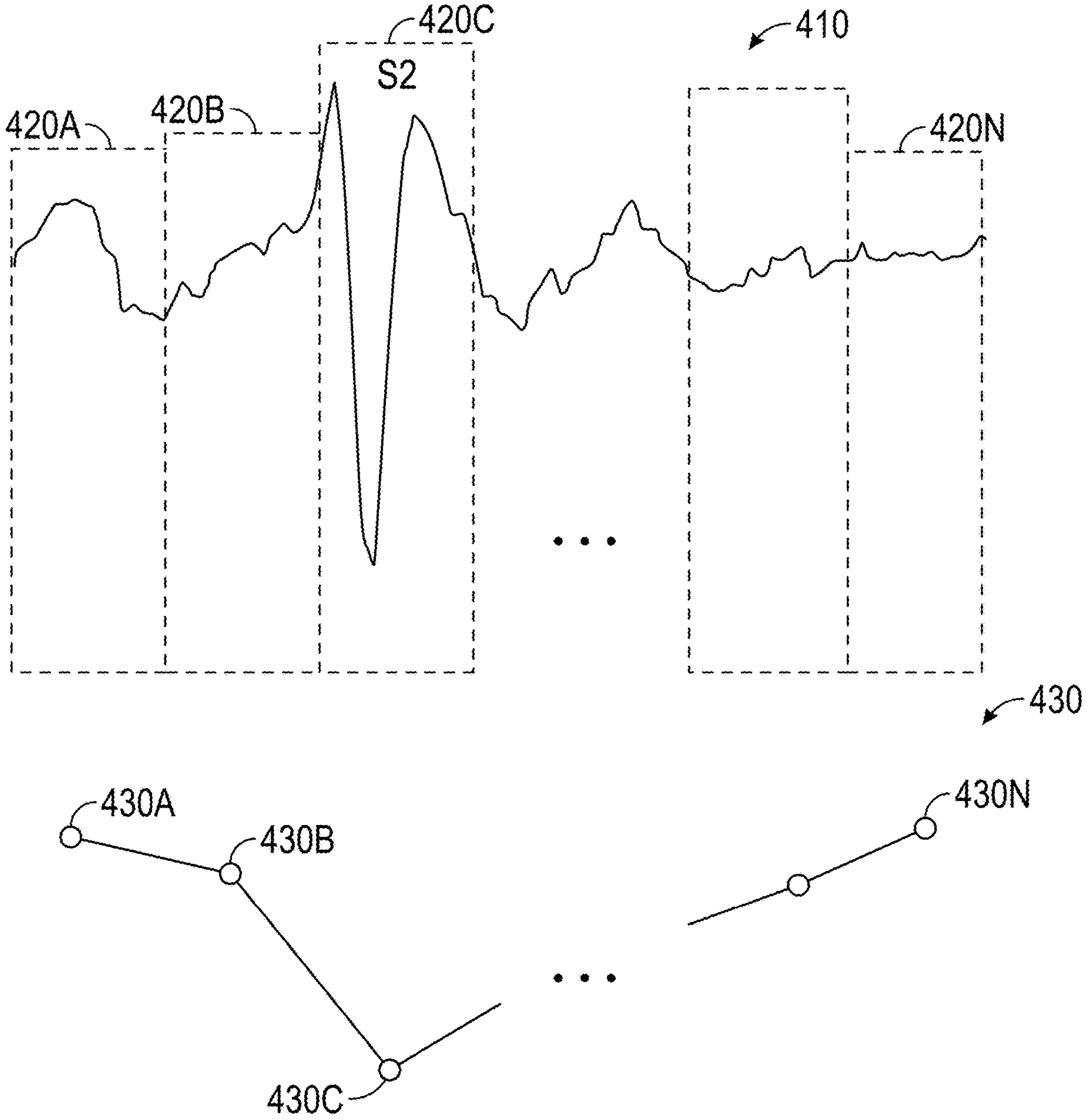
FIG. 4 illustrates generally an example of a spectral entropy time series generated from a representative heart sound segment and detecting therefrom a heart sound component.

FIG. 4 illustrates generally an example of a spectral entropy time series generated from a representative, such as ensemble averaged, heart sound segment 410 and detecting therefrom a heart sound component. The ensemble averaged heart sound segment 410 can be partitioned into a plurality of heart sound data windows 420A, 420B, 420C, . . . , 420N, such as using a sliding time window moving from the beginning to the end of the ensemble averaged heart sound segment 410. Although the heart sound data windows shown in FIG. 4 are non-overlapped to each other, in some examples at least some of the heart sound data windows may be overlapped to each other. The size (length) of the sliding window and the amount of overlap can each have user-programmable values. The spectral entropy can be computed for each heart sound data window using the following equations:

$$S^m(w_k) = |X^m(w_k)|^2 \quad (1)$$

$$P_k^m = \frac{s^m(w_k)}{\sum_{j=1}^{w} s^m(w_j)} \quad (2)$$

$$SE(m) = -\sum_{k=1}^{L} P_k^m \log(P_k^m) \quad (3)$$

where Equation (1) calculates the power spectrum $S^m(w_k)$ of the heart sound data window $w_k$, using Fourier transform (e.g., discrete Fourier transform, or fast Fourier transform) $X^m(w_k)$ of $w_k$; Equation (2) estimates the probability distribution of the power spectrum $S^m(w_k)$, and Equation (3) computes the spectral entropy SE (m), where m represents the window index, and L the total number of HS data windows.

Spectral entropy values can be computed respectively for each of the heart sound data windows 420A, 420B, 420C, . . . , 420N. The resulting spectral entropy values 430A, 430B, 430C, . . . , 430N can be concatenated with respect to respective timings of the data windows 420A, 420B, 420C, . . . , 420N (such as the center of respective heart sound windows as shown herein) to form a spectral entropy time series 430. By way of example and not limitation, FIG. 4 shows only one spectral entropy value for each heart sound data window. In some examples, a sequence of multiple spectral entropy values may be computed for each heart sound data window. In an example, the spectral entropy sequence may have the same time resolution as the original heart sound signal, such that when the spectral entropy values 430A, 430B, 430C, . . . , 430N are concatenated, the resulting spectral entropy time series 430 may have the same number of data points as the representative heart sound segment 410.

Figure 5:
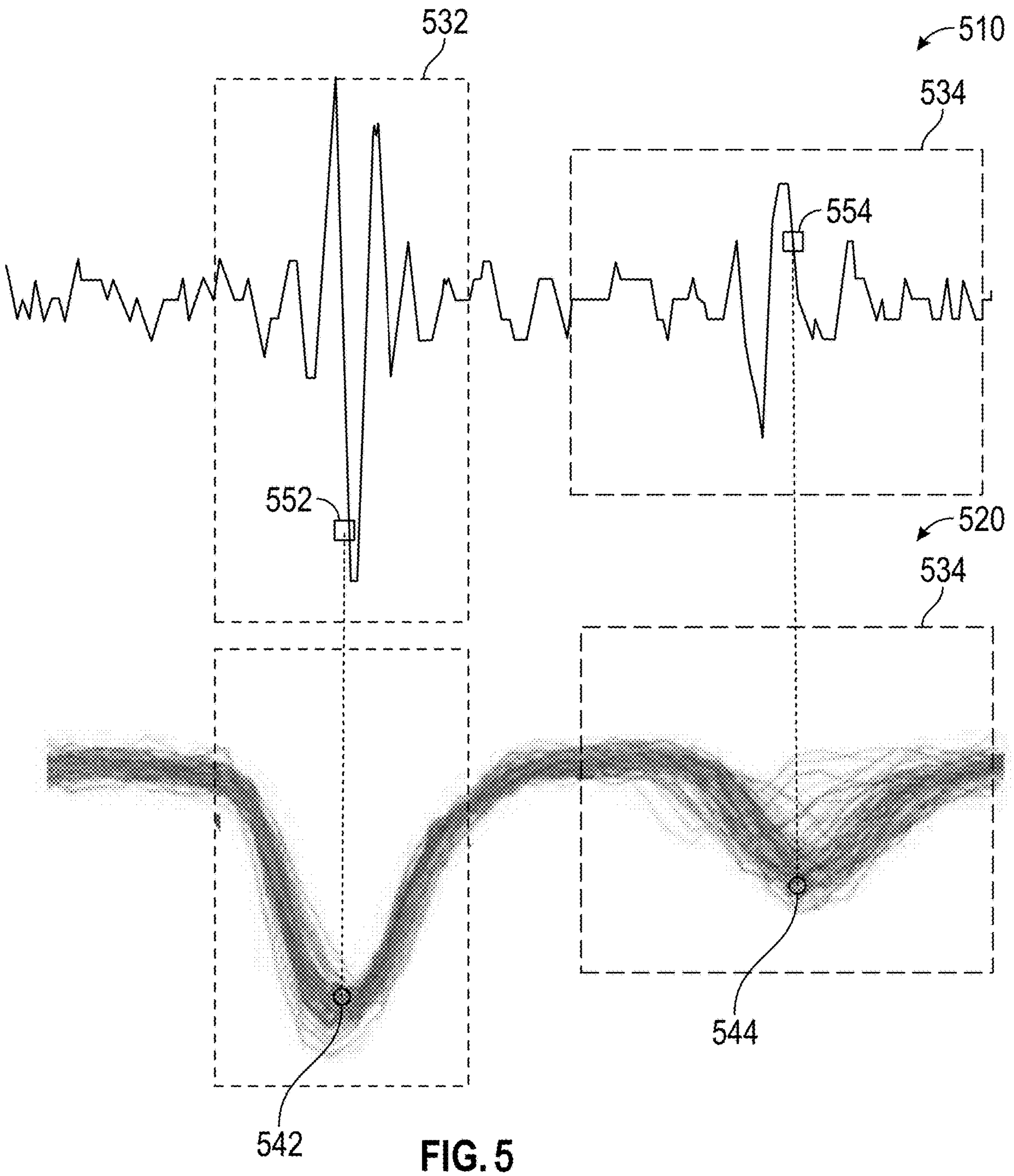
FIG. 5 illustrates an overlay plot of multiple spectral entropy time series each generated from respective representative heart sound segments.

FIG. 5 illustrates generally an example of an overlay plot of multiple spectral entropy time series 520 each generated from respective representative (e.g., ensemble-averaged) heart sound segments, one of which is shown as a representative heart sound segment 510. The representative heart sound segments all correspond to substantially the same heart rate (within a margin of, e.g., +/−5 bpm) or within the same heart rate range. The spectral entropy time series can be generated using the approach as described above with reference to FIG. 4. In the example shown in FIG. 5, the heart sound signal is bandpass-filtered to approximately 30-100 Hz, and the spectral entropy is calculated for heart sound data windows created using a sliding window of 20 samples long (at the original heart sound sampling rate) with an overlap of 16 samples. Other window length or overlap may be used. The spectral entropy time series 520, each having a finer data resolution than the spectral entropy time series 430 as shown in FIG. 4, can be temporally aligned with the representative heart sound segment 510 with respect to respective timings of the heart sound data windows. An S1 detection window 532 is then applied to the spectral entropy time series 520, and a local minimum 542 within the S1 detection window 532 is detected and recognized as S1. Likewise, an S2 detection window 534 is applied to the spectral entropy time series 520, and a local minimum 544 within the S2 detection window 534 is detected and recognized as S2. As the multiple spectral entropy time series 520 are temporally aligned with the representative heart sound segment 510, S1 amplitude 552 and S2 amplitude 554 can each be determined from the representative heart sound segment 510 based on the locations of the local minimum 542 and local minimum 544, respectively.

Figure 6A:
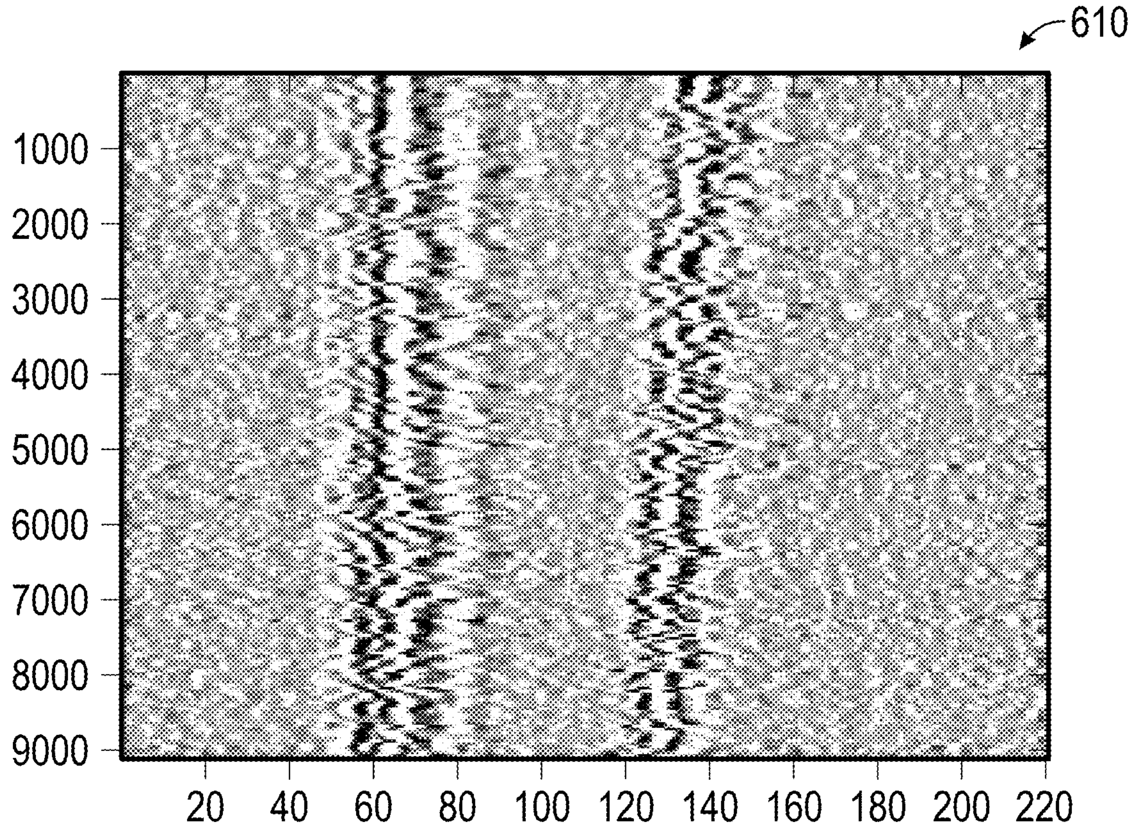
FIGS. 6A-6D illustrate examples of spectral entropy-based heart sound tracking under different signal-to-noise ratios (SNR) of heart sound signals.
Figure 6B:
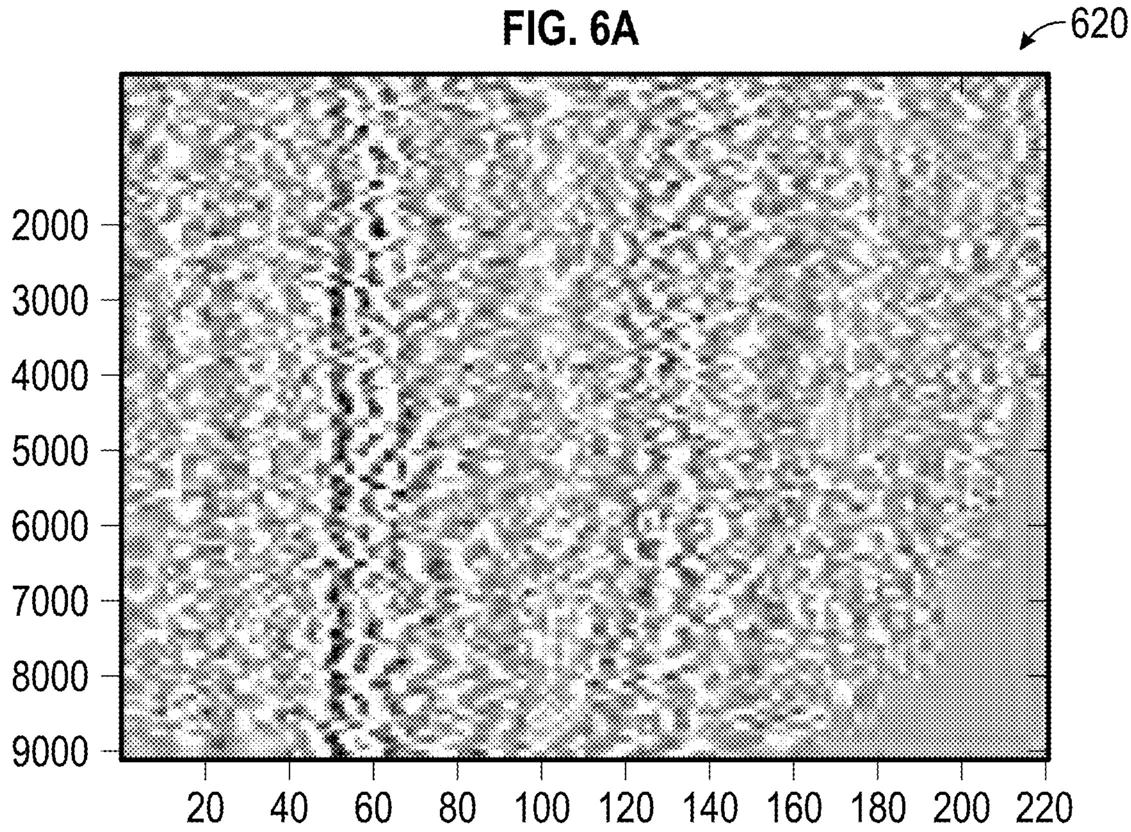
Figure 6C:
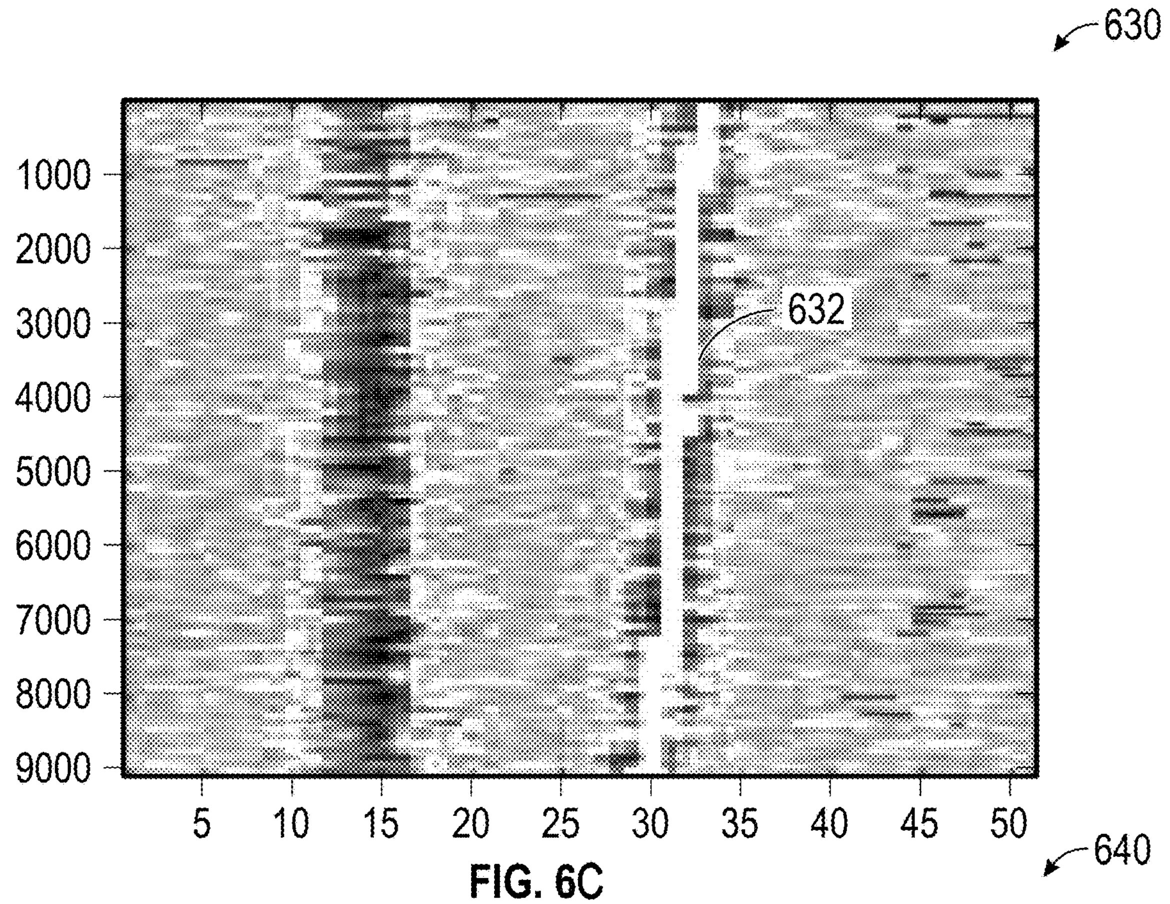
Figure 6D:
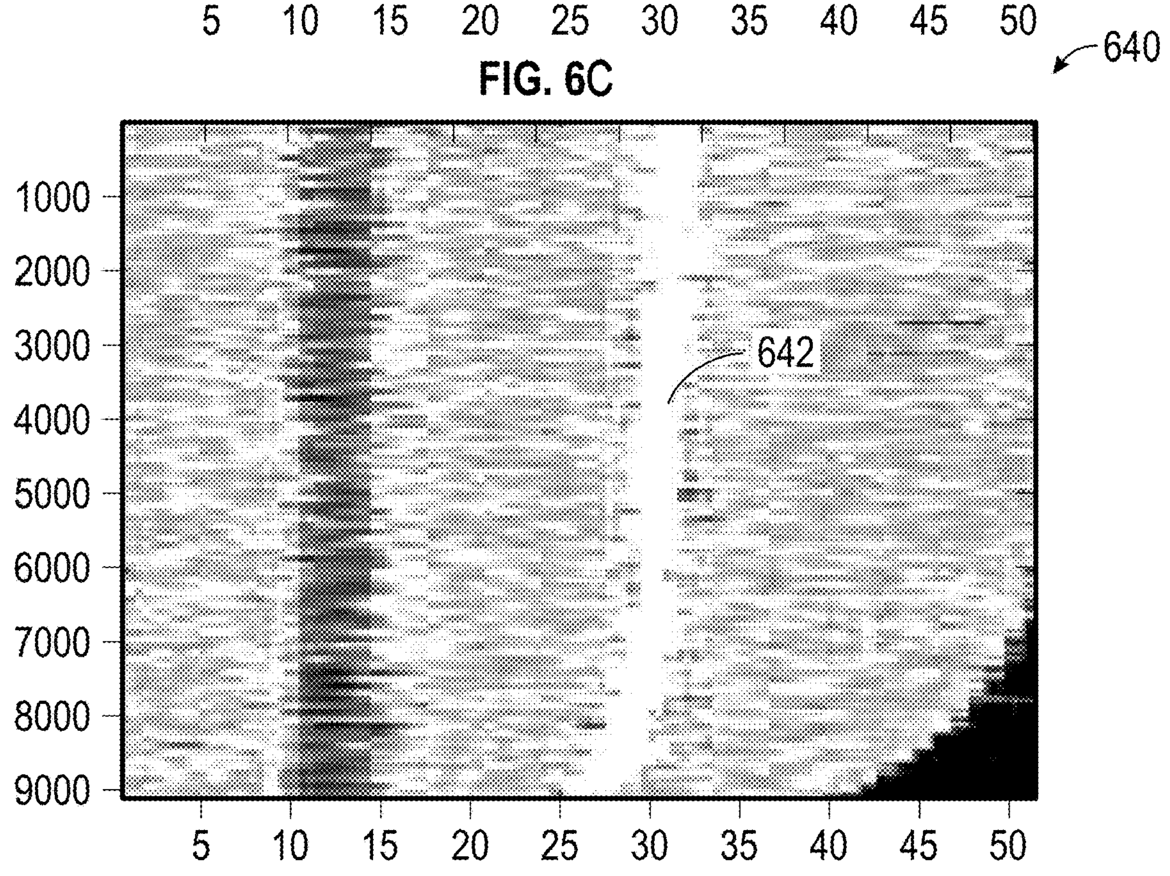

FIGS. 6A-6D illustrate spectral entropy-based heart sound tracking under different signal-to-noise ratios (SNR) of heart sound signals. FIG. 6A illustrates a heart sound map 610 at a high SNR, and FIG. 6B illustrates a heart sound map 620 at a low SNR. A heart sound map represents a plurality of heart sound segments stacked together (along the y-axis, indexed by the number of segments). The plurality of heart sound segments are extracted from multiple cardiac cycles with varying heart rates, and aligned with respect to a fiducial point (the origin of the x-axis), such as the R wave of respective cardiac cycle. Each heart sound segment (on the x-axis) has the signal amplitudes color-coded or gray scale-coded to show the changes in amplitude over time. At low SNR as shown in FIG. 6B, certain heart sound components, such as S2, becomes faded, indicating lower and irregular S2 amplitudes. Detecting S2 in such low SNR environment can be challenging when using a time-domain, amplitude-based heart sound recognition method. FIG. 6C illustrates a spectral entropy map 630 generated from the heart sound map 610, and FIG. 6D illustrates a spectral entropy map 640 generated from the heart sound map 620. A spectral entropy map represents a plurality of spectral entropy time series, each calculated from the corresponding heart sound segments within a cardiac cycle, that are stacked along the y-axis and indexed by the number of heart sound segments. Each spectral entropy time series (on the x-axis, time) has the spectral entropy values color-coded or gray scale-coded to show the changes in spectral entropy over time. Heart sound components, particularly S1 and S2, can be detected from each spectral entropy time series based on, for example, local minima in respective S1 detection window and S2 detection window, as described above with reference to FIGS. 2 and 3A-3B. To track the heart sound components, the detected heart sound components from the multiple stacked spectral entropy time series can be connected to show a heart sound component trend, such as an S2 trend 632 in FIG. 6C, or an S2 trend 642 in FIG. 6D. As illustrated in FIGS. 6C and 6D, the entropy-based approach as descried in this document can accurately recognize heart sound components (e.g., S2) and track their changes over time at variable heart rates even in the presence of low SNR in the raw heart sound signal.

Figure 7:
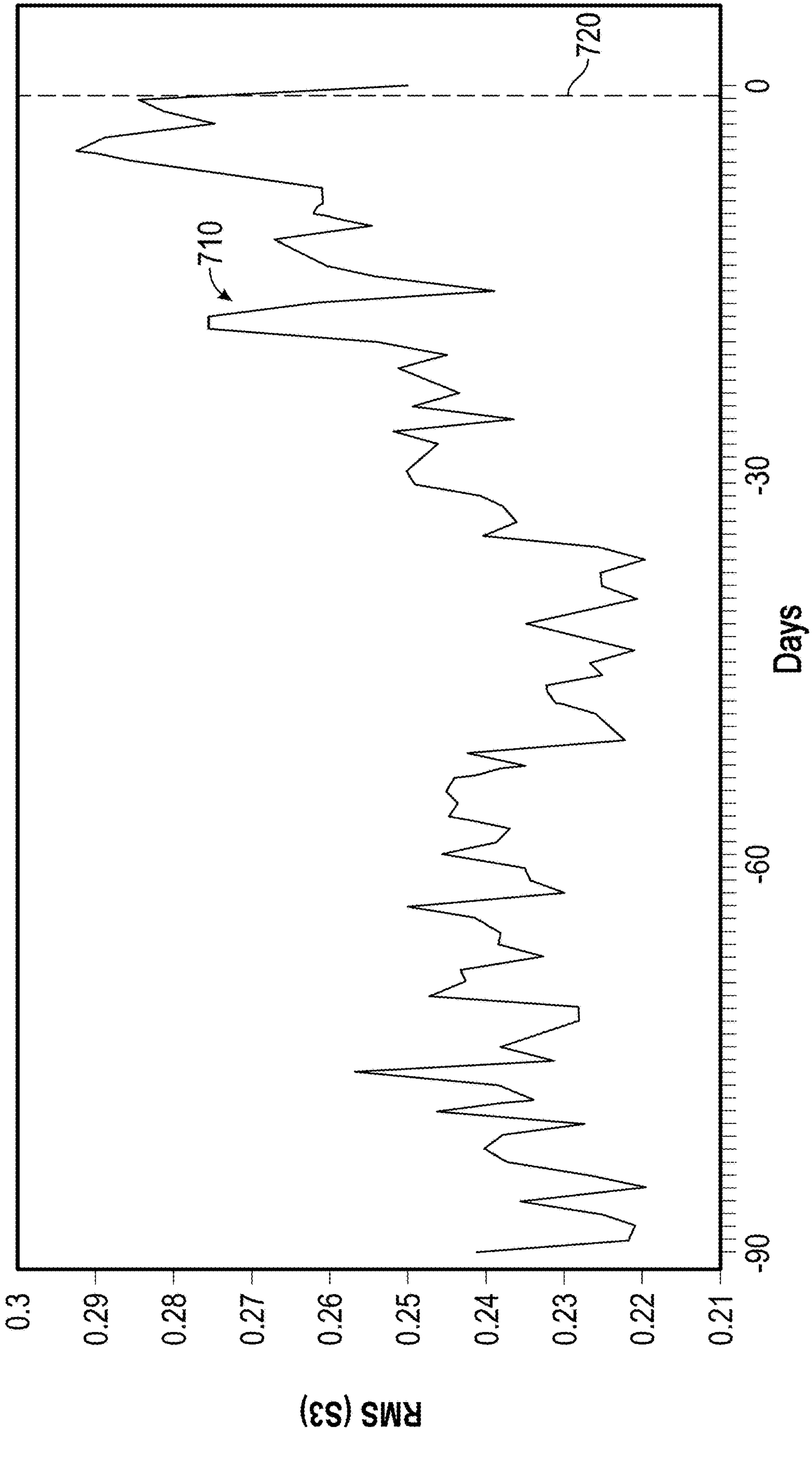
FIG. 7 illustrates generally an example of detecting worsening heart failure (WHF) based at least in part on spectral entropy-based recognition and tracking of S3 heart sounds.

FIG. 7 illustrates generally an example of detecting worsening heart failure (WHF) based at least in part on spectral entropy-based recognition and tracking of S3 heart sounds. From each cardiac cycle, S3 can be detected based the timing of S2 detected within that cardiac cycle using the entropy-based approach as described above. In an example, S3 can be detected within a S3 detection window that begins at the S2 timing, or a specified offset following the detected S2 (e.g., approximately 50-125 msec following the S2 timing) and lasts a duration of approximately 125 msec. An S3 metric, such as a root-mean-square (RMS) of S3, can be computed and tracked over time, as represented by a daily S3 trend 710. An WHF detection index can be computed using S3 RMS value, optionally along with other sensor information, through a weighted combination unit or other types of sensor fusion engine. In this example, daily S3 is tracked for approximately 90 days until the WHF detection index value reaches and exceeds a predetermined WHF detection threshold, at which point (time zero 720) an WHF event is deemed detected, and a user can be alerted. In an example, the WHF detection index may include an intensity (e.g., amplitude or RMS value) ratio of S3 to S1 components. Pramodsingh et al. U.S. patent application Ser. No. 15/473,783 entitled "SYSTEMS AND METHODS FOR DETECTING WORSENING HEART FAILURE" describes techniques for detecting worsening cardiac events such as WHF events using information from multiple sensors including heart sounds, the disclosure of which is incorporated by reference herein in its entirety.

Figure 8:
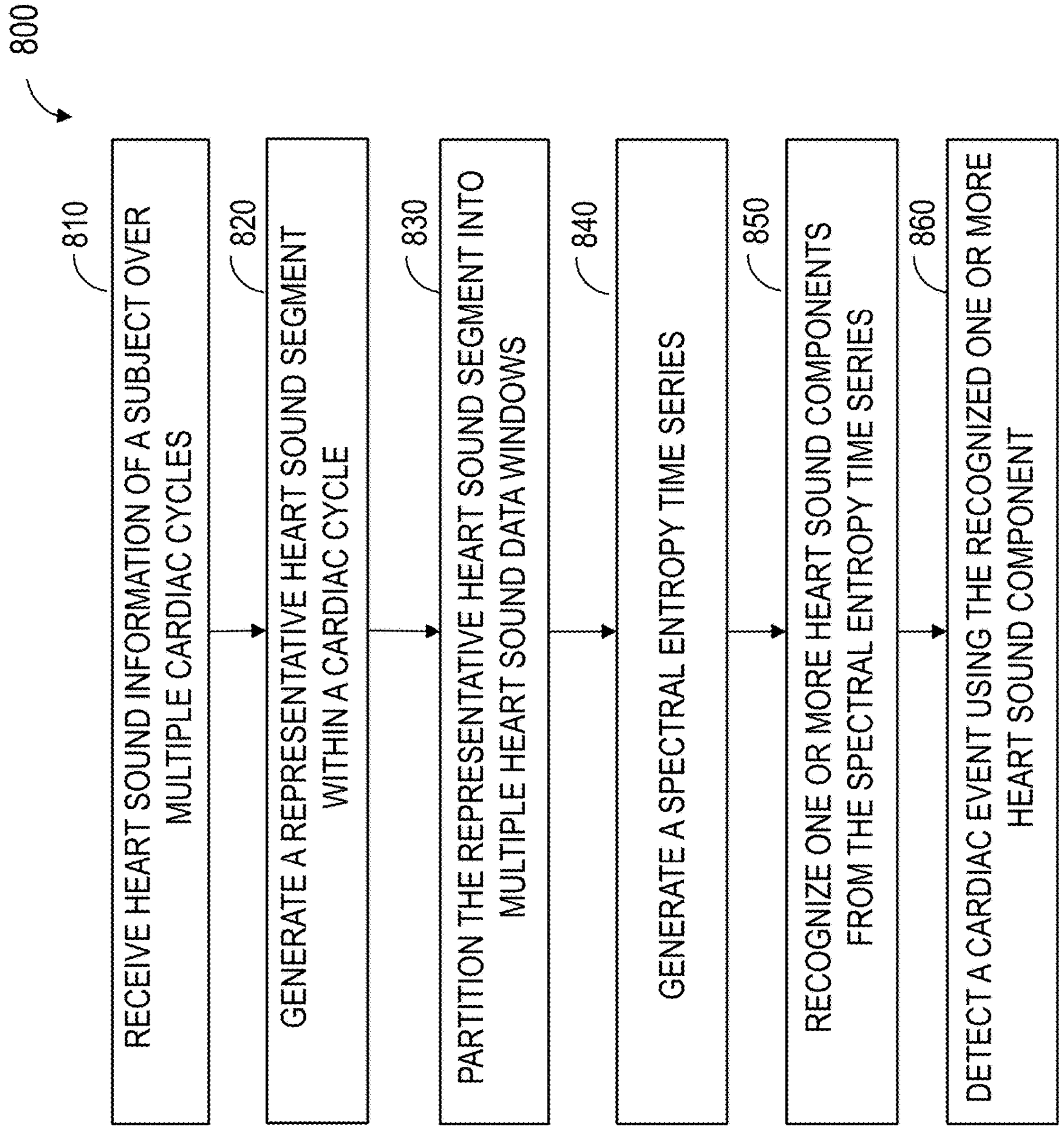
FIG. 8 illustrates generally an example of a method for recognizing and tracking a heart sound component from a heart sound signal and using the recognized heart sound component to detect a physiologic event.

FIG. 8 illustrates generally an example of a method 800 for recognizing and tracking a heart sound component from a heart sound signal and using the recognized heart sound component to detect a physiologic event. The method 800 may be implemented and executed in an ambulatory medical device such as an implantable or wearable medical device, or in a remote patient management system. In an example, the method 800 may be implemented in and executed by the IMD 102 or the WMD 103, the external system 105, or the heart sound-based physiologic event detection system 200.

The method 800 begins at 810 to receive physiologic information of a subject including heart sounds over multiple cardiac cycles. The heart sounds may be detected using a sensor associated with or included in an ambulatory or wearable device. In some examples, endocardial acceleration signals sensed from inside the heart may be used to analyze heart sounds. Other physiologic information may also be received, including a cardiac electrical signal such as an electrocardiography (ECG) or an intracardiac electrogram (EGM), heart rate, signals indicative of cardiac mechanical activity including, for example, thoracic or cardiac impedance signal, arterial pressure signal, pulmonary artery pressure signal, left atrial pressure signal, RV pressure signal, LV pressure signal, heart sounds or endocardial acceleration signal, physiologic response to activity, apnea hypopnea index, one or more respiration signals such as a respiration rate signal or a tidal volume signal, among others.

At 820, a representative heart sound segment may be generated using at least a portion of the received heart sounds. An example of the representative heart sound segment is an ensemble average of a plurality of heart sound segments taken from respective cardiac cycles, and time-aligned with respect to respective fiducial points, such as R waves in the multiple cardiac cycles of an ECG signal. In some examples, a subset of the heart sound segments that satisfy a specified condition are selected and used to establish the representative heart sound segment. The selection criterion may include one or more of patient activity level, heart rate, respiration rate, or time of a day, among other conditions. For example, a subset of the heart sound segments corresponding to substantially the same cycle length (e.g., within a margin of +/−100 milliseconds) or substantially the same heart rate (e.g., within a margin of +/−5 beats per minute) can be selected and used to establish the representative heart sound segment. In another example, a subset of the heart sound segments sensed during substantially the same time period of a day (e.g., within a specific margin) can be selected and used to establish the representative heart sound segment.

At 830, the representative heart sound segment can be partitioned into multiple heart sound data windows using a sliding time window. The heart sound data windows can be non-overlapped to each other. Alternatively, at least some of the heart sound data windows may be overlapped to each other. The size (length) of the sliding window and the amount of overlap can each have user-programmable values. The spectral entropy can be computed for each heart sound data window using Equations (1) through (3), such as described above with reference to FIG. 4. At 840, the spectral entropy values respectively calculated for the heart sound data windows can be concatenated with respect to respective timings of the data windows to form a spectral entropy time series.

At 850, one or more heart sound components, including S1 or S2 components, may be recognized from the spectral entropy time series, such as using the heart sound component detector 328 as described above with reference to FIGS. 3A-3B. In an example, an S1 component can be recognized as a local minimum of a portion of the spectral entropy time series within an S1 detection window. Similarly, an S2 component can be recognized as a local minimum of a portion of the spectral entropy time series within an S2 detection window. The S1 and S2 time windows can have user-programmable locations and sizes (lengths). By way of example and not limitation, the S1 detection window may begin at 50 milliseconds (msec) following a detected R wave on an ECG signal and have a duration of 300 msec. An S2 detection window can begin at specified offset following a detected R wave or S1 heart sound. Other heart sound components, such as S3, can be detected from the spectral entropy time series or a heart sound energy signal within a detection window (e.g., an S3 detection window) defined based on the timings of the S1 or S2 components. By way of example and not limitation, an S3 detection window may begin at the S2 timing, or a specified offset following the detected S2 (e.g., approximately 50-125 msec following the S2 timing), a last a duration of approximately 125 msec.

In some examples, the recognition of heart sound components (e.g., S1 or S2) can be based on heart rate-dependent heart sound spectral entropy templates previously generated and stored in a template database. Each template may include one or more of a spectral entropy time series $SE_T$, spectral entropy values of heart sound components such as S1 and S2, or S1 and S2 timings with respect of a fiducial point such as R wave, all determined at a specific heart rate or heart rate range. Instantaneous heart rate concurrently sensed with the heart sound information over the multiple cardiac cycles can then be used to query the template database to identify (or select) therefrom a heart rate-matched template with a corresponding heart rate or heart rate range that matches the instantaneous heart rate. One or more heart sound components can then be detected using the selected heart rate-matched template. In an example, instead of the representative heart sound segment and the spectral entropy time series respectively generated at steps 820 and 840, only the heart rate-matched template is used to generate various heart sound components. In another example, the spectral entropy time series generated at step 840 from the representative HS segment, can be modified by the heart rate-matched spectral entropy time series stored in the heart rate-matched spectral entropy template. The modification may include, for example, taking an average of the spectral entropy time series of the representative heart sound segment and the heart rate-matched spectral entropy time series stored in the heart rate-matched spectral entropy template. One or more heart sound components can then be detected from the modified spectral entropy time series. In some examples, the heart rate-matched spectral entropy template in the database can be updated with the modified spectral entropy time series.

At 860, a cardiac event may be detected using the one or more heart sound components, such as using the physiologic event detector 224. The physiologic event may include an indicator of myocardial contractility, cardiac synchrony, and cardiac hemodynamics, a cardiac arrhythmia episode, or a WHF event. In some examples, the heart sound metric may be used together with other sensor information to detect respiratory, renal, neurological, among other medical conditions, based on the heart sound metrics generated from the heart sound segment. In some examples, based on the detection of the physiologic event, a recommendation may be generated and provided to the user. The recommendation may include one or more of further diagnostic tests to be performed, adjustment of one or more parameters for detecting the physiologic event, or therapy to be delivered or adjustment of one or more therapy parameters. The system user may review and adjudicate the detected physiologic event, and reprogram one or more detection or therapy parameters, such as using the user interface 230. In some examples, therapy may be delivered to the patient in response to the detected physiologic event, such as via the therapy circuit 240 as illustrated in FIG. 2. Examples of the therapy may include electrostimulation therapy delivered to the heart, a nerve tissue, other target tissues, a cardioversion therapy, a defibrillation therapy, or drug therapy including delivering drug to a tissue or organ. In some examples, an existing therapy or treatment plan may be modified to treat the detected arrhythmia, such as modify patient follow-up schedule, or adjust a stimulation parameter or drug dosage.

Figure 9:
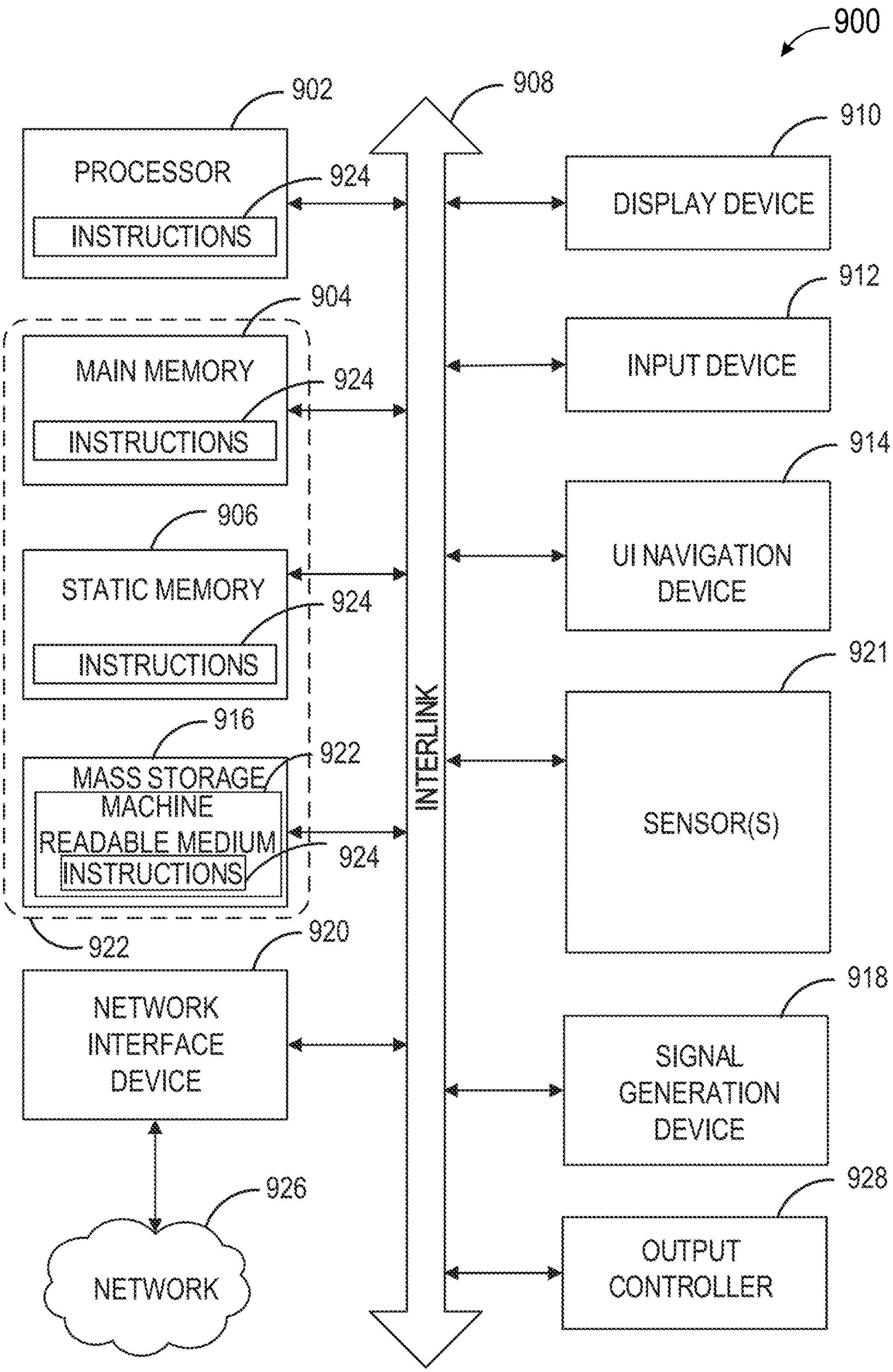
FIG. 9 illustrates generally a block diagram of an example machine upon which any one or more of the techniques (e.g., methodologies) discussed herein may perform.

FIG. 9 illustrates generally a block diagram of an example machine 900 upon which any one or more of the techniques (e.g., methodologies) discussed herein may perform. Portions of this description may apply to the computing framework of various portions of the IMD 102, the WMD 103, the external system 105, or the heart sound-based physiologic event detection system 200.

In alternative embodiments, the machine 900 may operate as a standalone device or may be connected (e.g., networked) to other machines. In a networked deployment, the machine 900 may operate in the capacity of a server machine, a client machine, or both in server-client network environments. In an example, the machine 900 may act as a peer machine in peer-to-peer (P2P) (or other distributed) network environment. The machine 900 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 900 may include a hardware processor 902 (e.g., a central processing unit (CPU), a graphics processing unit (GPU), a hardware processor core, or any combination thereof), a main memory 904 and a static memory 906, some or all of which may communicate with each other via an interlink (e.g., bus) 908. The machine 900 may further include a display unit 910 (e.g., a raster display, vector display, holographic display, etc.), an alphanumeric input device 912 (e.g., a keyboard), and a user interface (UI) navigation device 914 (e.g., a mouse). In an example, the display unit 910, input device 912 and UI navigation device 914 may be a touch screen display. The machine 900 may additionally include a storage device (e.g., drive unit) 916, a signal generation device 918 (e.g., a speaker), a network interface device 920, and one or more sensors 921, such as a global positioning system (GPS) sensor, compass, accelerometer, or other sensor. The machine 900 may include an output controller 928, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 916 may include a machine readable medium 922 on which is stored one or more sets of data structures or instructions 924 (e.g., software) embodying or utilized by any one or more of the techniques or functions described herein. The instructions 924 may also reside, completely or at least partially, within the main memory 904, within static memory 906, or within the hardware processor 902 during execution thereof by the machine 900. In an example, one or any combination of the hardware processor 902, the main memory 904, the static memory 906, or the storage device 916 may constitute machine readable media.

While the machine-readable medium 922 is illustrated as a single medium, the term "machine readable medium" may include a single medium or multiple media (e.g., a centralized or distributed database, and/or associated caches and servers) configured to store the one or more instructions 924.

The term "machine readable medium" may include any medium that is capable of storing, encoding, or carrying instructions for execution by the machine 900 and that cause the machine 900 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EPSOM)) and flash memory devices; magnetic disks, such as internal hard disks and removable disks; magneto-optical disks; and CD-ROM and DVD-ROM disks.

The instructions 924 may further be transmitted or received over a communication network 926 using a transmission medium via the network interface device 920 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 920 may include one or more physical jacks (e.g., Ethernet, coaxial, or phone jacks) or one or more antennas to connect to the communication network 926. In an example, the network interface device 920 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 900, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

What is claimed is:

1. A medical-device system, comprising:
- a data receiver circuit configured to receive heart sound information; and
- a heart sound recognition circuit configured to:
  - generate a representative heart sound segment within a cardiac cycle using at least a portion of the received heart sound information;
  - partition the representative heart sound segment into multiple heart sound data windows;
  - calculate spectral entropy values respectively for each of the multiple heart sound data windows; and
  - determine one or more heart sound components including an S2 component using the calculated spectral entropy values.

2. The medical-device system of claim 1, wherein the heart sound recognition circuit is configured to:
- partition the representative heart sound segment into the multiple heart sound data windows using a sliding time window;
- generate a spectral entropy time series by concatenating the calculated spectral entropy values in accordance with respective timings of the multiple heart sound data windows; and
- determine the one or more heart sound components including the S2 component using the spectral entropy time series.

3. The medical-device system of claim 2, wherein the heart sound recognition circuit is configured to determine the S2 component based on a local minimum of a portion of the spectral entropy time series within an S2 detection window.

4. The medical-device system of claim 3, wherein the data receiver circuit is configured to receive (i) a cardiac electrical signal and (ii) information about instantaneous heart rates, both of which are concurrently sensed with the heart sound information, wherein the heart sound recognition circuit is configured to determine the S2 detection window using ventricular activations on the cardiac electrical signal and the instantaneous heart rates.

5. The medical-device system of claim 2, wherein the heart sound recognition circuit is configured to:

generate, and store in a memory, one or more heart rate or rhythm dependent heart sound spectral entropy templates each including a spectral entropy time series of a heart sound at a particular heart rate or rhythm; and determine the one or more heart sound components further using the one or more heart rate or rhythm dependent heart sound spectral entropy templates.

6. The medical-device system of claim 5, wherein the data receiver circuit is configured to receive information about an instantaneous heart rate or rhythm concurrently sensed with the heart sound information, wherein the heart sound recognition circuit is configured to:

select one of the stored one or more heart rate or rhythm dependent heart sound spectral entropy templates with a corresponding heart rate or rhythm that matches the instantaneous heart rate or rhythm; and determine the one or more heart sound components using the selected stored heart rate or rhythm dependent heart sound spectral entropy template.

7. The medical-device system of claim 6, wherein the heart sound recognition circuit is configured to:

modify the spectral entropy time series of the representative heart sound segment with the selected stored heart rate or rhythm dependent heart sound spectral entropy template; and determine the one or more heart sound components using the modified spectral entropy time series of the representative heart sound segment.

8. The medical-device system of claim 7, wherein to modify the spectral entropy time series of the representative heart sound segment, the heart sound recognition circuit is configured to compute an average of (i) the spectral entropy time series of the representative heart sound segment and (ii) the spectral entropy time series in the selected stored heart rate or rhythm dependent heart sound spectral entropy template.

9. The medical-device system of claim 7, wherein the heart sound recognition circuit is configured to update the selected stored heart rate or rhythm dependent heart sound spectral entropy template in the memory with the modified spectral entropy time series of the representative heart sound segment.

10. The medical-device system of claim 2, wherein the heart sound recognition circuit is configured to:

calculate the spectral entropy values using Fourier transform-based frequency-domain analysis; and determine the S2 component based on detecting that a local minimum of the spectral entropy time series within the S2 detection window falls below a spectral entropy floor representing spectral entropy values outside of the S2 detection window, the S2 component corresponding to a narrowband signal having concentrated energy in a frequency range of approximately 20-70 Hz.

11. The medical-device system of claim 1, wherein the portion of the received heart sound information includes a plurality of heart sound segments taken respectively from multiple cardiac cycles, wherein the heart sound recognition circuit is configured to:

time-align the plurality of heart sound segments with respect to respective fiducial points for the multiple cardiac cycles of a cardiac electrical signal concurrently sensed with the heart sound information; and generate the representative heart sound segment using an ensemble average of the time-aligned plurality of heart sound segments.

12. The medical-device system of claim 1, wherein the data receiver circuit is configured to receive information about instantaneous heart rates concurrently sensed with the heart sound information over multiple cardiac cycles, wherein the portion of the received heart sound information over the multiple cardiac cycles used for generating the representative heart sound segment corresponds to substantially identical instantaneous heart rates or within a pre-determined heart rate range.

13. The medical-device system of claim 1, wherein the heart sound recognition circuit is further configured to detect an S3 component or an S4 component from the representative heart sound segment based at least in part on timing information of the determined S2 component.

14. The medical-device system of claim 1, further comprising a physiological event detector configured to detect a cardiac event using the determined one or more heart sound components.

15. The medical-device system of claim 1, wherein:

the data receiver circuit comprises an accelerometer configured to sense epicardial or endocardial acceleration signals containing components corresponding to heart sound vibrations; and the medical-device system is configured as one of an implantable cardiac monitor or a wearable medical device.

16. A method of recognizing a heart sound component, comprising:

receiving heart sound (HS) information;

generating a representative heart sound segment within a cardiac cycle using at least a portion of the received heart sound information;

partitioning the representative heart sound segment into multiple heart sound data windows;

calculating spectral entropy values respectively for each of the multiple heart sound data windows; and determining one or more heart sound components including an S2 component using the calculated spectral entropy values.

17. The method of claim 16, comprising receiving information about heart rates concurrently sensed with the heart sound information over multiple cardiac cycles, wherein the portion of the received heart sound information over the multiple cardiac cycles used for generating the representative heart sound segment corresponds to substantially identical heart rates or within a pre-determined heart rate range.

18. The method of claim 17, wherein determining the one or more heart sound components includes:

generating a spectral entropy time series by concatenating the calculated spectral entropy values in accordance with respective timings of the multiple heart sound data windows; and determining the one or more heart sound components including the S2 component based on a local minimum of a portion of the spectral entropy time series within an S2 detection window.

19. The method of claim 17, comprising:

generating and storing in memory one or more heart rate or rhythm dependent heart sound spectral entropy templates each including a spectral entropy time series of a heart sound at a particular heart rate or rhythm; and determine the one or more heart sound components further using the one or more heart rate or rhythm dependent heart sound spectral entropy templates.

20. The method of claim 19, comprising:

receiving information about a heart rate or rhythm concurrently sensed with the heart sound information over multiple cardiac cycles;

selecting one of the stored one or more heart rate or rhythm dependent heart sound spectral entropy templates with a corresponding heart rate or rhythm that matches the heart rate or rhythm; and determine the one or more heart sound components using the selected stored heart rate or rhythm dependent heart sound spectral entropy template.

* * * * *